(12) United States Patent
Lyons et al.

(10) Patent No.: US 10,124,172 B2
(45) Date of Patent: Nov. 13, 2018

(54) APPARATUS AND METHODS FOR PREVENTION OF SYNCOPE

(71) Applicants: NATIONAL UNIVERSITY OF IRELAND, GALWAY, Galway (IE); Declan Lyons, Limerick (IE); Colin Quinn, Galway (IE)

(72) Inventors: Declan Lyons, Limerick (IE); Colin Quinn, Galway (IE); Gearóid Ó Laighin, Ennis (IE); Paul Breen, Emly (IE); Brian Deegan, Ennis (IE); Fabio Quondamatteo, Máigh Cuilinn (IE)

(73) Assignees: National University of Ireland, Galway, Galway (IE); Declan Lyons, Limerick (IE); Colin Quinn, Galway (IE)

( * ) Notice: Subject to any disclaimer, the term of this patent is extended or adjusted under 35 U.S.C. 154(b) by 0 days.

(21) Appl. No.: 15/193,927

(22) Filed: Jun. 27, 2016

(65) Prior Publication Data

US 2016/0331974 A1 Nov. 17, 2016

Related U.S. Application Data

(62) Division of application No. 14/357,331, filed as application No. PCT/IE2012/000049 on Nov. 9, 2012, now Pat. No. 9,403,000.

(30) Foreign Application Priority Data

Nov. 11, 2011 (IE) .................................... 2011/0491

(51) Int. Cl.
*A61N 1/36* (2006.01)
*A61N 1/04* (2006.01)
(Continued)

(52) U.S. Cl.
CPC ........ *A61N 1/36139* (2013.01); *A61B 5/0205* (2013.01); *A61B 5/0245* (2013.01);
(Continued)

(58) Field of Classification Search
CPC ............ A61N 1/36585; A61N 1/36135; A61N 1/36542; A61N 1/08; A61N 1/365;
(Continued)

(56) References Cited

U.S. PATENT DOCUMENTS 5,725,562 A * 3/1998 Sheldon ............. A61N 1/36542
607/19
6,719,701 B2 4/2004 Lade
(Continued)

FOREIGN PATENT DOCUMENTS

EP 1331022 A2 7/2003

OTHER PUBLICATIONS

International Search Report; PCT/IE2012/000049; dated Feb. 11, 2013.
(Continued)

*Primary Examiner* — Deborah Malamud
(74) *Attorney, Agent, or Firm* — Studebaker & Brackett PC

(57) ABSTRACT

A monitoring system has biomechanical sensors, physiological sensors and a controller which receive sensory inputs from the sensors to provide output signals for the output device, and it detects from the sensory inputs risk of a syncopal event The bio-mechanical sensors include sensors arranged to allow the processor to detect a user postures and posture transitions. The processor operates a finite state machine, in which there is a state corresponding to each of a plurality of user physical postures and to each of a plurality of transitions between said postures, and the processor determines a relevant state depending on the sensory inputs.

(Continued)

A device output may be muscle stimulation to prevent syncope, and there are stimulation permissions associated with the finite state machine states.

3 Claims, 16 Drawing Sheets

(51) Int. Cl.
| | |
|---|---|
| *A61N 1/365* | (2006.01) |
| *A61B 5/0245* | (2006.01) |
| *A61B 5/0205* | (2006.01) |
| *A61B 5/0402* | (2006.01) |
| *A61B 5/0488* | (2006.01) |
| *A61B 5/00* | (2006.01) |
| *A61N 1/372* | (2006.01) |
| *A61N 1/378* | (2006.01) |
| *A61N 1/05* | (2006.01) |
| *A61B 5/11* | (2006.01) |
| *A61B 5/08* | (2006.01) |
| *A61B 5/024* | (2006.01) |

(52) U.S. Cl.
CPC .......... *A61B 5/0402* (2013.01); *A61B 5/0488* (2013.01); *A61B 5/1116* (2013.01); *A61B 5/1117* (2013.01); *A61B 5/7275* (2013.01); *A61N 1/0452* (2013.01); *A61N 1/0456* (2013.01); *A61N 1/0484* (2013.01); *A61N 1/0556* (2013.01); *A61N 1/36003* (2013.01); *A61N 1/365* (2013.01); *A61N 1/3606* (2013.01); *A61N 1/36014* (2013.01); *A61N 1/36535* (2013.01); *A61N 1/36542* (2013.01); *A61N 1/3787* (2013.01); *A61N 1/37229* (2013.01); *A61B 5/024* (2013.01); *A61B 5/08* (2013.01); *A61B 5/0816* (2013.01); *A61B 5/1123* (2013.01); *A61B 2562/0219* (2013.01)

(58) Field of Classification Search
CPC .............. A61N 1/3702; A61N 1/36535; A61N 1/3621; A61N 1/3606; A61N 1/36167; A61N 1/3704; A61N 1/37223; A61N 1/0408; A61N 1/36003; A61N 1/37; A61N 1/0484; A61B 5/1123; A61B 5/4519; A61B 5/6807; A61B 5/684; A61M 2230/04; A61M 2230/60; A61M 2230/63; A61F 5/0111; A61H 2205/12
See application file for complete search history.

(56) References Cited

U.S. PATENT DOCUMENTS

| | | | |
|---|---|---|---|
| 7,593,776 B2 * | 9/2009 | Loeb ................ | A61N 1/36003 375/222 |
| 2003/0199943 A1 | 10/2003 | Katz et al. | |
| 2008/0139899 A1 | 6/2008 | Student et al. | |
| 2008/0140137 A1 | 6/2008 | Wall, III et al. | |
| 2009/0270748 A1 | 10/2009 | Corbucci et al. | |

OTHER PUBLICATIONS

International Preliminary Report on Patentability; PCT/IE2012/000049; dated May 13, 2014.

* cited by examiner

Posterior View    Anterior View

APPARATUS AND METHODS FOR PREVENTION OF SYNCOPE

FIELD OF THE INVENTION

The invention relates to the prevention of syncope.

PRIOR ART DISCUSSION

Syncope the medical term for fainting, is precisely defined as a transient loss of consciousness and postural tone, characterised by rapid onset, short duration, and spontaneous recovery, due to global cerebral hypoperfusion (low blood flow to the brain) that most often results from hypotension (low blood pressure). The term syncope excludes seizures, coma, shock, or other states of altered consciousness.

Syncope is a prevalent disorder and accounts for 1-3% of emergency department (ED) visits and up to 6% of hospital admissions each year in the United States, due to the injuries sustained when the person falls on fainting. In fact, about 33% of syncopal episodes result in injuries and some of these injuries can be quite severe, such as hip fractures. Syncope may lead to physical disability and subsequent functional decline.

A leading cause of syncope is Orthostatic Hypotension (OH), which is defined as a sustained drop in blood pressure exceeding 20 mmHg systolic or 10 mmHg diastolic occurring within 3 minutes of assuming upright posture. On average, approximately 500 ml to 1000 ml of blood is transferred to the abdomen and legs after transition to upright standing (Lipsitz 1989). This causes a reduction in venous return to the heart, leading to a decrease in cardiac output and blood pressure. In healthy people, stretch receptors in the aortic arch and carotid arteries detect the reduction in blood pressure, and trigger an increase in sympathetic and a decrease in parasympathetic outflow from the central nervous system. This results in an increase in heart rate and systemic vascular resistance, thereby restoring blood pressure. Failure of these compensatory mechanisms leads to excessive pooling of blood in the abdomen and legs, thereby causing orthostatic hypotension. This can result in reduced blood flow to the brain, causing dizziness, nausea, syncope, or falls.

Another prevalent cause of syncope is neurocardiogenic syncope, which is characterised by the development of arterial vasodilatation, with or without a sudden decrease in heart rate. The exact mechanisms of neurocardiogenic syncope have not yet been identified. Some studies have demonstrated increased pooling of blood in the peripheral circulation (Glick and Yu 1963), as well as decreased skeletal muscle tone (Hargreaves and Muir 1992) in patients with neurocardiogenic syncope. Other potential causes include neuro-hormonal abnormalities, reduced blood volume, and abnormalities in blood pressure regulatory mechanisms (Mosqueda-Garcia et al. 2000).

Excessive pooling of blood resulting in syncope also occurs in patients with postural orthostatic tachycardia syndrome (POTS). POTS is a condition defined as an abnormal increase in heart rate during standing (a sustained increase in heart rate of 30 beats per minute or a sustained heart rate reading greater than 120 beats per minute). POTS patients experience a marked reduction in thoracic blood volume and excessive pooling of blood in the lower limbs during upright posture, leading to symptoms including palpitations, fatigue, chest discomfort, exercise intolerance, and dizziness. 25% of POTS patients develop syncope during prolonged tilt (Carew et al. 2009).

Preventing Syncope

The body's natural mechanism to promote venous return to the heart from the lower limbs is based on muscular contraction of the lower limbs. It is generally accepted that contraction of the posterior musculature, typically during walking, compresses the deep veins of the lower limb and aids venous blood return to the heart. This mechanism is known as the calf muscle pump. However, during prolonged quiet standing, the muscle pump is inactive. Without the activity of the muscle pump, pooling of blood in the lower limbs and abdomen can occur, increasing the risk of fainting and subsequent falls-related injuries.

Current prevention options for syncope are limited. The gold standard non-pharmalogical treatment is to prescribe the use of graduated compression stockings by the patients. These stockings compress the legs, thereby limiting pooling of blood in the deep veins of the leg. However, these stockings are difficult to put on and take off, are uncomfortable, and in clinical practice, are poorly tolerated by patients.

Patients are often prescribed drugs to increase systemic vascular resistance, or to expand blood volume. While such drugs are often effective, they can lead to an unsafe rise in blood pressure, particularly while the patient is lying down. This problem is exacerbated by the fact that hypertension is common in elderly patients with orthostatic intolerance.

Cardiac Pacing

A number of alternative techniques for the prevention of syncope have been suggested. One such technique is the use of cardiac pacing to increase heart rate and blood pressure to prevent OH and syncope. Both U.S. Pat. Nos. 5,913,879 and 66,620,467 describe a system that detects a change in posture (combined with a blood pressure drop as in U.S. Pat. No. 66,620,467), and deliver cardiac pacing to prevent OH. A number of systems, including those described in US20040862831, WO2004US11498, and US 2002004672 trigger cardiac pacing to prevent Syncope when a significant drop in heart rate is detected. The system described in US20020132044 analyses cardiac contractility to detect impending syncope and trigger cardiac pacing. WO2010030942 and WO2003US01714 describe similar systems, which use respiratory data to detect impending syncope and deliver cardiac pacing.

Treatment of syncope using cardiac pacing has to date shown mixed results. This is because syncope can occur without a significant drop in heart rate (vasodepressor syncope). Also, the heart can only pump the blood that it receives, and if venous return falls drastically due to venous pooling, then increased heart rate and/or contractility may not be sufficient to restore cardiac output and blood pressure.

Drug Delivery/Vagus Nerve Stimulation

In US20070255330, a system is described that includes multiple implanted physiological sensors, including ECG and EEG. These sensors can be used either to gather data via a telemetric link (including syncope/seizure episodes), or to synchronise delivery of a therapy. Therapy may include drug delivery, or stimulation comprised of at least one of electrical, thermal, optical, chemical, mechanical, and magnetic stimulation. Examples described include NMES stimulation to prevent sleep apnoea, and a system of implanted stimulators to correct drop-foot.

US2007027497 describes a system that stimulates the vagus nerve if blood pressure drops below a threshold value. WO2004095306 describes a system that estimates the probability that a patient will experience a syncopal event. This system is triggered by detection of posture change, and estimates the likelihood of syncope based on autonomic nervous system activity. If the probability of syncope exceeds a threshold, then a therapy is delivered (cardiac pacing or drug delivery).

Augmented Venous Return

In U.S. Pat. No. 7,519,426, a system is described where a change in posture is detected, and cardiac output is increased by stimulating the phrenic nerve. In US20040204663, a system is described that improves blood flow in the lower limbs by applying vibration in the 10-120 Hz range to the soles of the subject's feet, thereby increasing venous return. A displacement sensor is also worn on the leg, and vibration is only applied when the displacement sensor indicates no movement of the leg.

In U.S. Pat. No. 6,282,448 a system is described that applies NMES stimulation to the calf muscle to improve blood flow and prevent OH. Footswitches have been described for drop foot correction as described in U.S. Pat. No. 7,632,239.

WO2008091227 and WO2010105045 describe fall-detection systems is claiming detection of a fall for purposes such as collection of ECG and respiration data at the time of the syncope.

US2007027497 uses electrical stimulation of a sympathetic (and/or para-sympathetic) nerve such that the patient's blood pressure is increased to a sufficient level to prevent syncope. This targets stimulation of the autonomic nervous system.

US201025670s describes a system that prevents flight related G-force induced loss of consciousness using neuro-muscular electrical stimulation of the abdomen and lower extremities during flight. This invention uses very large G-forces to trigger NMES in a fighter cockpit.

REFERENCES

Carew, S., M. O. Connor, J. Cooke, R. Conway, C. Sheehy, A. Costelloe and D. Lyons (2009). "A review of postural orthostatic tachycardia syndrome." Europace 11(1): 18-25.
Glick, G. and P. N. Yu (1963). "Hemodynamic changes during spontaneous vasovagal reactions." Am J Med 34: 42-51.
Hargreaves, A. D. and A. L. Muir (1992). "Lack of variation in venous tone potentiates vasovagal syncope." Br Heart J 67(6): 486-90.
Lipsitz, L. A. (1989). "Orthostatic hypotension in the elderly." N Engl J Med 321(14): 952-7.
Mosqueda-Garcia, R., R. Furlan, J. Tank and R. Fernandez-Violante (2000). "The elusive pathophysiology of neurally mediated syncope." Circulation 102(23): 2898-906.

SUMMARY OF THE INVENTION

According to the invention, there is provided a monitoring system comprising:
at least one biomechanical sensor,
at least one physiological sensor,
output devices, and
a controller having a signal conditioning circuit and a processor arranged to receive sensory inputs from the sensors and to execute algorithms to provide output signals for the output device, and
wherein the processor is adapted to detect from the sensory inputs risk of a syncopal event and to provide output signals for preventing a syncopal event from occurring.

In one embodiment, the bio-mechanical sensors include sensors arranged to allow the processor to detect a user posture.

In one embodiment, the bio-mechanical sensors include sensors arranged to allow the processor to detect a user posture transition.

In one embodiment, the bio-mechanical sensors include sensors arranged to allow the processor to detect a user walking. In one embodiment, the bio-mechanical sensors include sensors arranged to allow the processor to detect a user leg activity. Preferably, the physiological sensors include sensors (601), arranged to allow the processor to detect user heart rate. In one embodiment, the physiological sensors include sensors arranged to allow the processor to detect user respiration rate.

In one embodiment, the sensors comprise one or more selected from accelerometers, electrocardiography (ECG) sensors, electromyography (EMG) sensors, piezoelectric sensors, gyroscopes, flex sensors, strain gauges, foot switches, smart textiles incorporating electrical sensing elements. In one embodiment, at least one sensor is injectable.

In one embodiment, the sensors comprise an electrocardiography (ECG) sensor arranged to adhere to a user's chest, a hip-worn kinematic sensor incorporating a triaxial accelerometer and gyroscope, and at least one foot switch arranged to be incorporated into the insole of an article of footwear. In one embodiment, the system comprises a plurality of bio-mechanical sensors and the processor is adapted to use signals from said sensors to determine risk of syncope of the OH syncope type.

Preferably, the processor is adapted to use sensor signals from both a kinematic sensor and foot-switch to determine an intention to change posture according to trunk inclination, trunk angular velocity and force applied at the heels and toes.

In one embodiment, the processor is adapted to combine the bio-mechanical sensing of angular velocity, trunk inclination, heel contact force, toe contact force, with the physiological sensing of heart rate for determining risk of POTS-type syncope. In one embodiment, the processor is adapted to use sensor signals from posture-detecting bio-mechanical sensors and a heart rate sensor physiological sensor to determine risk of NCS-type syncope.

In one embodiment, the system comprises a plurality of bio-mechanical sensors and the processor is adapted to use signals from said sensors to determine risk of syncope of the OH syncope type, and to simultaneously in real time use signals from a combination of bio-mechanical and physiological sensors to determine risk of syncope of the NCS and/or POTS types.

In one embodiment, the output device comprises at least one muscle stimulator for applying muscle stimulation, and the processor is adapted to drive said stimulation means in response to the output data in order to prevent a syncopal event. Preferably, the muscle stimulator comprises a programmable neuromuscular electrical stimulation (NMES) device.

In one embodiment, the NMES device includes electrodes embedded within a compressive garment. In one embodiment, the electrodes are connected in the stimulator via electrically conductive fabric woven into the garment.

In one embodiment, the garment is adapted to be worn on at least one of the lower leg, the thigh, or the abdomen. In one embodiment, the garment facilitates placement of at least one of the electrodes on a limb at a location relative to an anatomical landmark such as the lateral aspect of the distal femoral head.

In one embodiment, the output devices include a neuromuscular electrical stimulation (NMES) device arranged to be implanted in a user. In one embodiment, the implantable neuromuscular electrical stimulation (NMES) device is injectable.

In one embodiment, the implantable neuromuscular electrical stimulation (NMES) device is arranged to deliver electrical stimulation to a target nerve via an implanted cable and a nerve cuff placed around the target nerve.

In one embodiment, the processor is adapted to terminate stimulation:
for OH syncope, standing for a specified duration has occurred or the patients starts walking,
for POTS syncope, after a specified time has elapsed, and
for neurocardiogenic syncope, when heart rate has restored to desired level.

In one embodiment, the system further comprises a radiofrequency (RF) coil arranged to be mounted on a fixed or mobile object such as a wall or furniture in order to perform ambient recharging of the stimulator. In one embodiment, the RF coil is adapted to be mounted in a bed and/or to a chair or other piece of appropriate furniture that would facilitate ambient re-charging.

In one embodiment, the processor is adapted to generate patient data including at least one of:
date and time when muscle stimulation was applied,
biomechanical or physiological event which triggered stimulation,
sensor data logged prior to stimulus being applied.

In one embodiment, the processor is also adapted to detect occurrence of a fall and to generate an alert to an output device to report the fall.

In one embodiment, the processor is adapted to log bio-mechanical and physiological data which occurred before the incidence of a fall.

In one embodiment, the processor is adapted to operate a finite state machine, in which there is a state corresponding to each of a plurality of user physical postures and to each of a plurality of transitions between said postures, and the processor determines a relevant state depending on the sensory inputs. Preferably, the states include a lying state, a lie-to-sit transition state, a state for sitting with feet horizontal, a state for sitting with feet on ground, a sit-to-stand transition state, and a standing state. The processor uses a range of sensory inputs, both bio-mechanical and physiological. In one embodiment, the processor operates in real time to minimise inadvertent application of NMES while also delivering NMES appropriately to prevent syncope. In one embodiment, each state has an associated muscle stimulation permission. Preferably, an intermediate stimulation level is associated with a state corresponding to the posture of sitting and a permission for a larger stimulation level for a state corresponding to the sit-to-stand transition. In one embodiment, there is a permission for zero stimulation for the state corresponding to a walking transition.

In one embodiment, the signal conditioning circuit comprises a low pass filter to eliminate rapid changes in these signals, which represent spurious activity, such as tapping the heel on the ground. In one embodiment, the cut-off frequency is n the region of 3 Hz to 7 Hz.

According to another aspect, there is provided a method for monitoring a patient, the method being performed by a monitoring system comprising at least one biomechanical sensor, at least one physiological sensor, output devices, and a controller having a signal conditioning circuit and a processor arranged to receive sensory inputs from the sensors and to execute algorithms to provide output signals controlling the output device,
wherein the method comprises the processor detecting from the sensory inputs risk of a syncopal event and providing output signals for preventing a syncopal event from occurring.

In one embodiment, the processor determines data including a user posture, a user posture transition, user walking, user leg activity, and user heart rate. In one embodiment, the processor receives and processes user respiration rate data. Preferably, the processor uses sensor signals from both a kinematic sensor and a foot-switch to determine an intention to change posture according to trunk inclination, trunk angular velocity and force applied at the heels and toes. In one embodiment, the processor is adapted to combine the bio-mechanical sensing of angular velocity, trunk inclination, heel contact force, toe contact force, with the physiological sensing of heart rate for determining risk of POTS-type syncope.

In one embodiment, the processor uses sensor signals from posture-detecting bio-mechanical sensors and a heart rate sensor physiological sensor to determine risk of NCS-type syncope. In one embodiment, the processor uses signals from said sensors to determine risk of syncope of the OH syncope type, and simultaneously in real time uses signals from a combination of bio-mechanical and physiological sensors to determine risk of syncope of the NCS and/or POTS types.

In one embodiment, the processor drives at least one muscle stimulator in response to the output data in order to prevent a syncopal event.

In one embodiment, the processor terminates stimulation:
for OH syncope, if standing for a specified duration has occurred or the patients starts walking,
for POTS syncope, after a specified time has elapsed, and
for neurocardiogenic syncope, when heart rate has restored to desired level.

In one embodiment, the controller generates patient data including at least one of:
date and time when muscle stimulation was applied,
biomechanical or physiological event which triggered stimulation,
sensor data logged prior to stimulus being applied.

In one embodiment, the processor also detects occurrence of a fall and generates an alert to an output device to report the fall.

In one embodiment, the processor logs bio-mechanical and physiological data which occurred before the incidence of a fall.

In one embodiment, the processor is adapted to operate a finite state machine, in which there is a state corresponding to each of a plurality of user physical postures and to each of a plurality of transitions between said postures, and the processor determines a relevant state depending on the sensory inputs.

In one embodiment, the states include a lying state, a lie-to-sit transition state, a state for sitting with feet horizontal, a state for sitting with feet on ground, a sit-to-stand transition state, and a standing state. The processor uses a range of sensory inputs, both bio-mechanical and physiological.

In one embodiment, the processor operates in real time to minimise inadvertent application of NMES while also delivering NMES appropriately to prevent syncope. In one embodiment, each state has an associated muscle stimulation permission. In one embodiment, an intermediate stimulation level is associated with a state corresponding to the posture of sitting and a permission for a larger stimulation level for a state corresponding too the sit-to-stand transition.

In one embodiment, there is a permission for zero stimulation for the state corresponding to a walking transition. In one embodiment, the method comprises the additional step of the controller low-pass filtering the sensory inputs to eliminate rapid changes in these signals, which represent spurious activity, such as tapping the heel on the ground. In one embodiment, the filtering is performed with a cut-off frequency in the range of 3 Hz to 7 hz.

In another aspect, the invention provides a computer readable medium comprising software code adapted to be executed by a digital processor to perform the processor steps of a method as defined in any embodiment above.

DETAILED DESCRIPTION OF THE INVENTION

The invention will be more clearly understood from the following description of some embodiments thereof, given by way of example only with reference to the accompanying drawings in which:—

Figure 11:
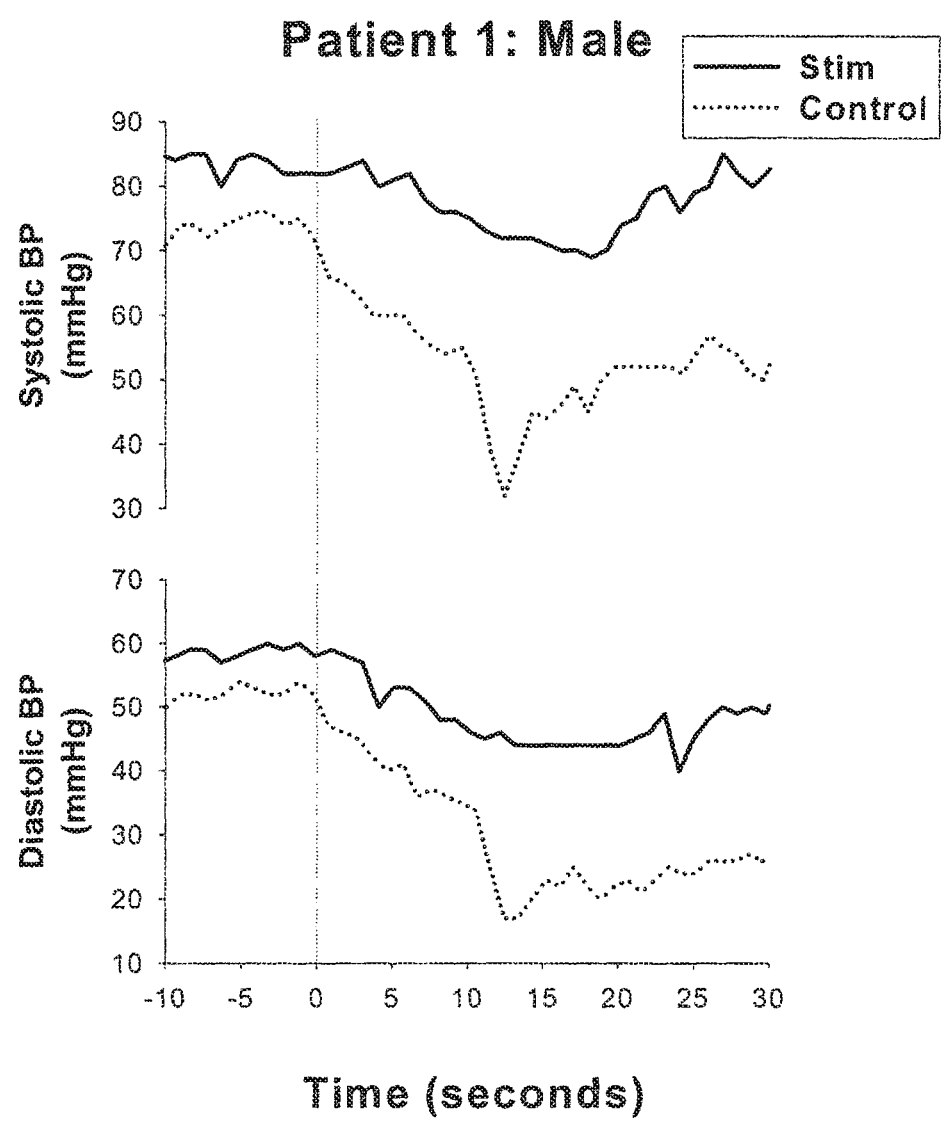
Figure 12A:
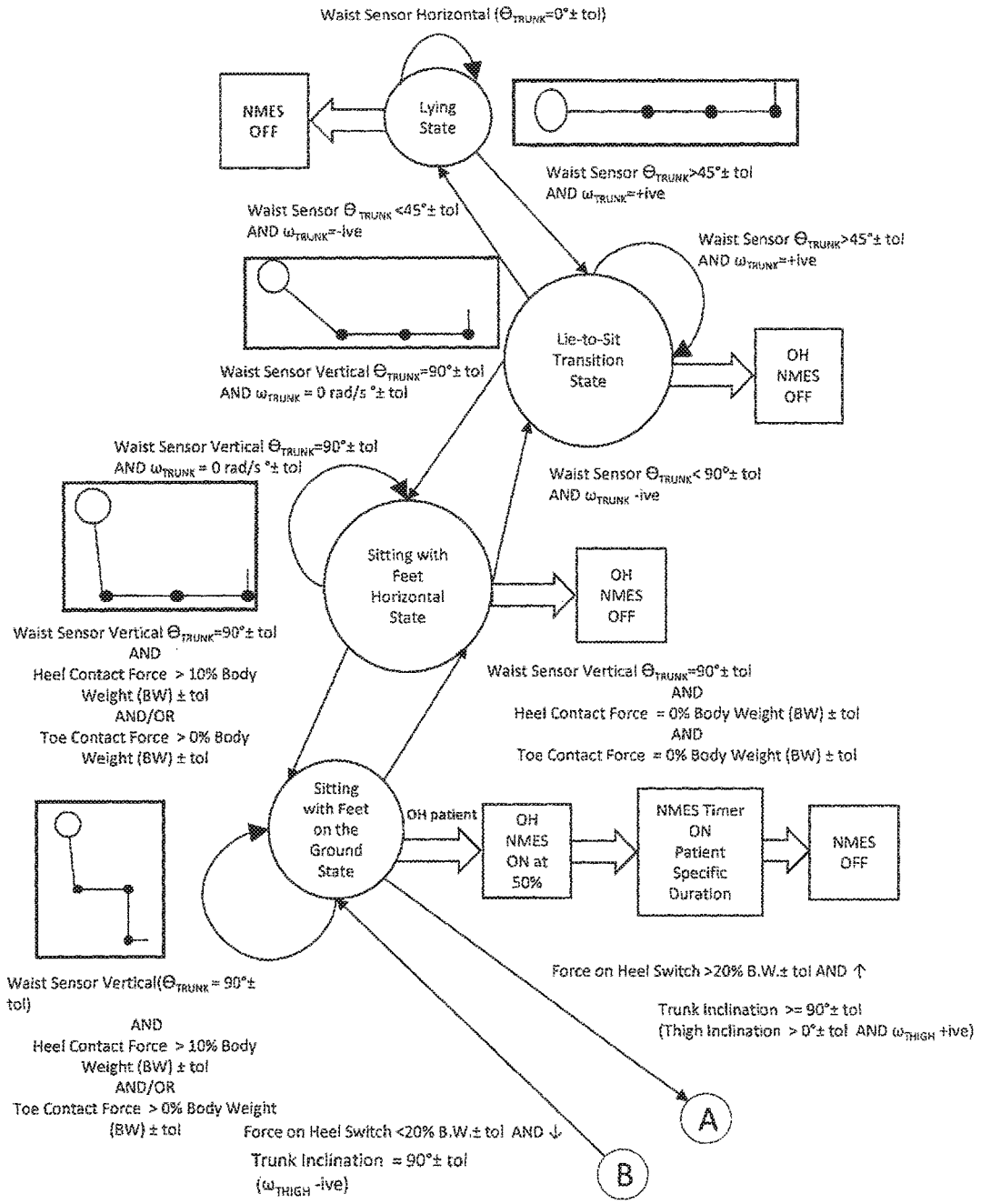
Figure 12B:
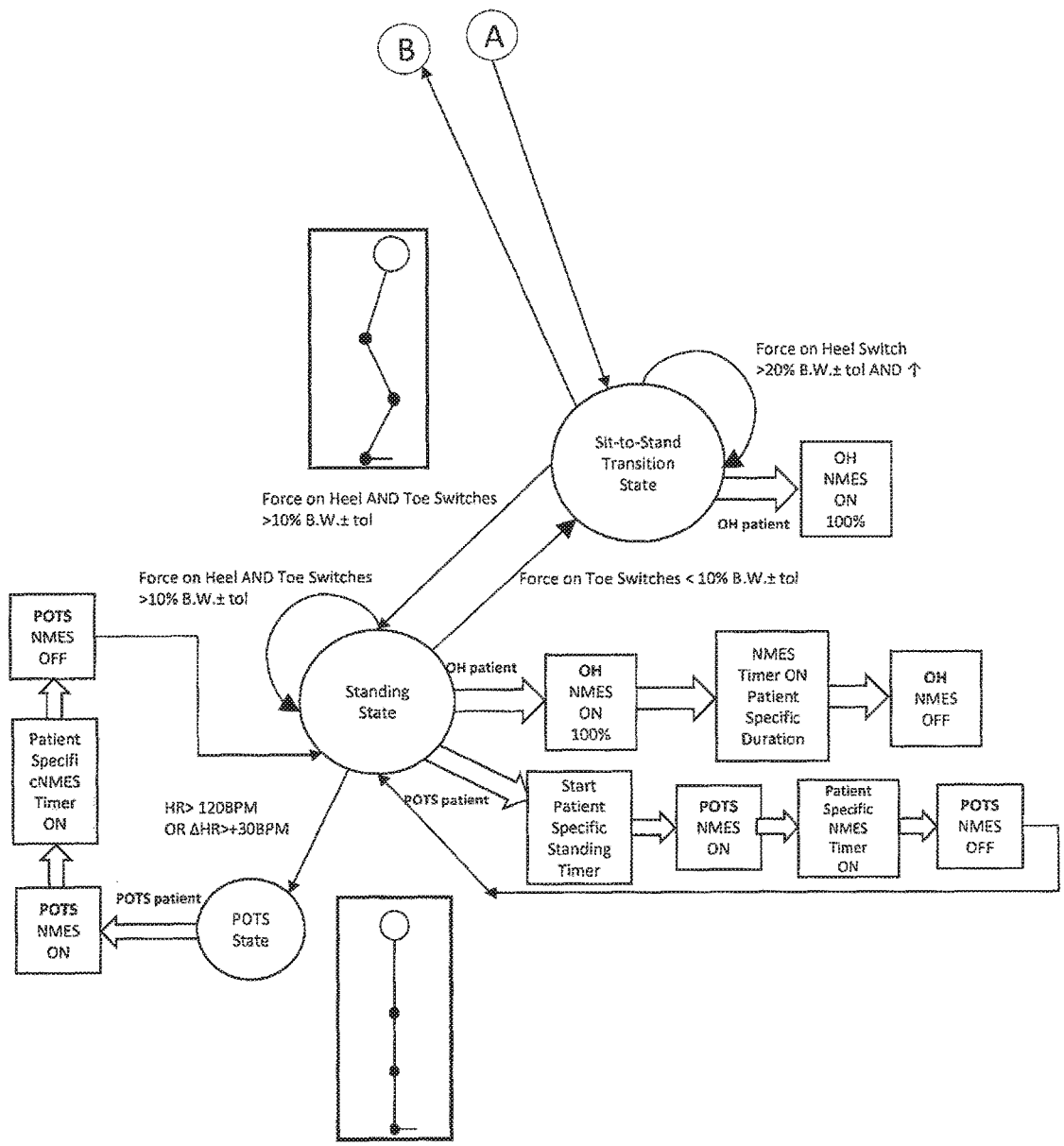

FIG. 11 demonstrates pilot data of Soleus muscle stimulation for prevention of OH; and FIGS. 12(a) and 12(b) are together a flow diagram for operation of a controller of a system of another embodiment.

DESCRIPTION OF THE EMBODIMENTS

Overview

Figure 1:
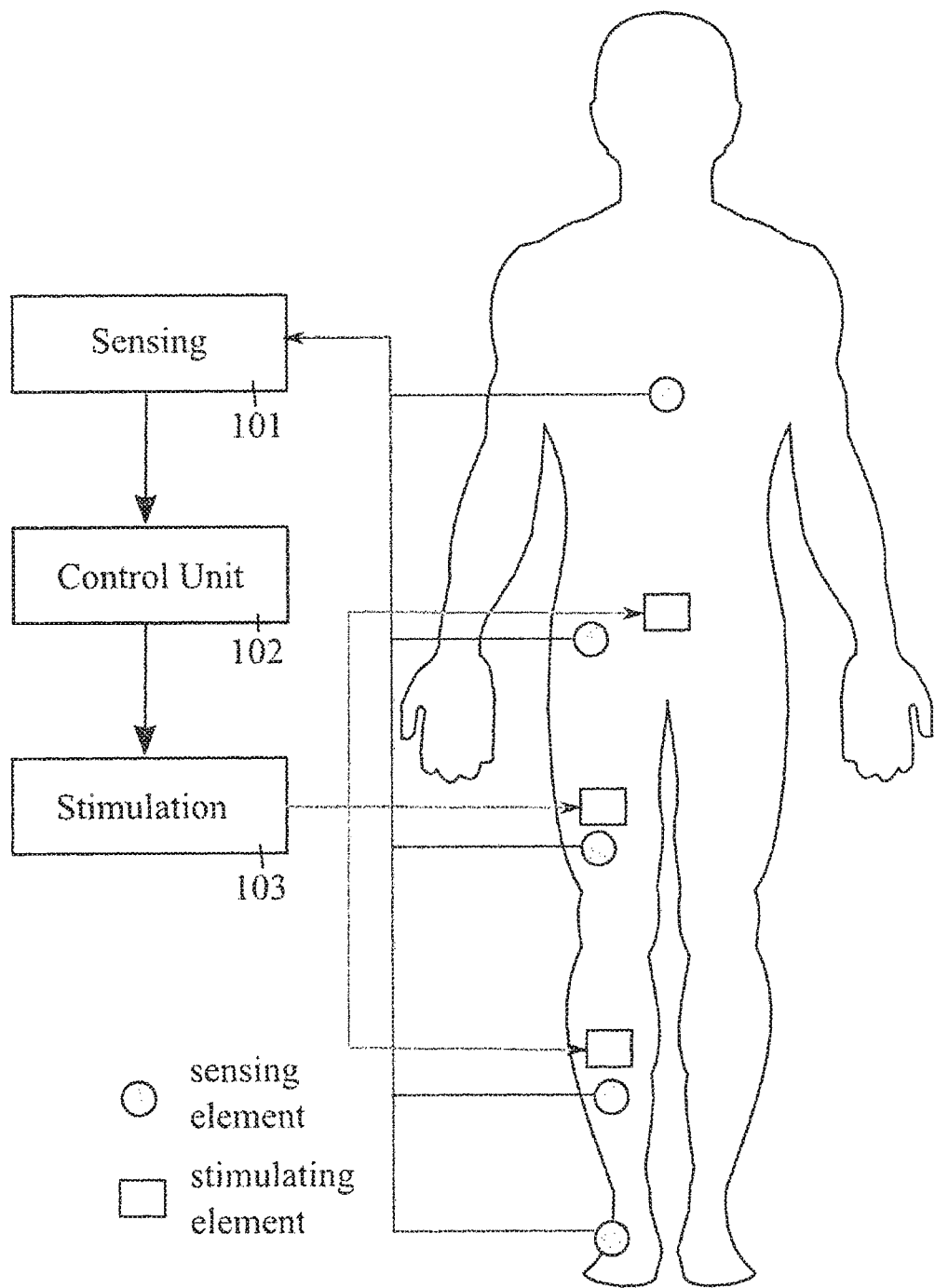
FIG. 1 shows an overview of the main elements of a system of the invention for syncope prevention.

Referring to FIG. 1 a system of the invention comprises sensors 101 of biomechanical and physiological events which can be related to the onset of a syncopal fall. A processor 102 is provided for analyzing sensed data, detecting risk of a syncopal fall, and tracking and reporting patient compliance and usage data. A muscle stimulation device 103 is provided for applying muscle stimulation to increase venous return in order to prevent a syncopal fall.

While the system has both bio-mechanical and physiological sensors it does not necessarily use them all for all predictions. The processor is programmed with the flexibility to process data from bio-mechanical sensors only to check for one type of syncopal risk, and to in real time also use a combination of bio-mechanical and physiological sensing to check for risk of a different syncopal type. The system generates an alert at least, or in some embodiments it takes an action to prevent the syncopal fall from occurring. For example, the embodiment of FIG. 8 relies only on bio-mechanical sensing, whereas that of FIG. 9 uses a combination of these two types of sensing, as described in more detail below.

In various embodiments the system of the invention detects combinations of intention to change posture, periods of prolonged standing, heart rate changes, and respiration rate changes that are precursor events to the start of a syncopal fall (a faint related fall). The posture change intentions include for example: intention to sit up from lying, intention to stand up from sitting, and intention to stand up from lying. The system may detect different postures (sitting, standing, lying) and walking—these are important also in the control of the applications of NMES for syncope prevention. While the purpose of the system is to prevent a syncopal fall occurring, an additional feature of the system of some embodiments is to detect falls that have occurred and to distinguish whether these falls are recoverable or not. The system is therefore effective in enabling a person to go about their daily life, and it may be a wearable system that a person could use while carrying out activities of daily living.

The invention may be applied to:

reduce or prevent symptoms of orthostatic intolerance,
reduce or prevent orthostatic hypotension,
reduce or prevent POTS, and/or
prevent neurocardiogenic syncope (NCS).

The invention of some embodiments elicits real-time, sensor-controlled, electrically activated venous return through neuromuscular electrical stimulation ("NMES") of the leg musculature for the purpose of preventing various syncopopal conditions associated with orthostatic intolerance including orthostatic hypotension syncope, neurocardiogenic syncope, postural orthostatic tachycardia syndrome, and other forms of syncope related to orthostatic intolerance. The invention achieves this in a manner that is minimally invasive for the patient, requires minimal intervention by the patient, and which has very high usability characteristics.

The invention uses our understanding of the muscle pump mechanism, in which contraction of muscles in the lower limb causes venous blood to be forced from the intramuscular and surrounding veins and to be propelled towards the heart. It provides effective systems for the real-time prevention of syncope that properly consider the usability issues associated with these systems, where there is a significant requirement that the system is discreet and does not impede the patient from carrying out their activities of daily living. There may be an implanted device that can be implanted in the patient using minimally invasive surgical techniques, or a wearable system that can be easily put on and taken off each day and which is designed to be as unobtrusive as possible.

Using multiple sensors allows improved accuracy of the detection of precursor events to syncope, reducing the number of false detections of syncope and thus improving the comfort of the patient and their acceptance of the system.

If the system combines the bio-mechanical sensing of trunk angular velocity, trunk inclination, heel contact force and toe contact force its detection accuracy of the pre-cursor events for OH syncope is particularly good. OH syncope is triggered by postural change and the preferred sensor inputs for this are an accelerometer-based trunk inclinometer, a gyro to measure trunk angular velocity, a heel switch to measure heel contact force, and a toe switch to measure toe contact force.

If the system combines the bio-mechanical sensing of angular velocity, trunk inclination, heel contact force, toe contact force (to determine standing and intention to assume a standing posture), with the physiological sensing of heart rate it has good detection accuracy of the pre-cursor events for POTS syncope as heart rate increases are observed in syncope arising from POTS.

Neurocardiogenic syncope is often accompanied by a sudden reduction in heart rate during standing thus using the bio-mechanical sensing of angular velocity, trunk inclination, heel contact force, toe contact force (to determine standing and intention to assume a standing posture), with the physiological sensing of heart rate, the system has good detection accuracy of the pre-cursor events for Neurocardiogenic Syncope (NCS).

In a preferred embodiment, the system is effective for predicting in real time any of the three main types of syncope, namely the OH, POTS, and neurocardiogenic (NCS) types which might arise at any time.

The Stimulator

The stimulator unit communicates with the control unit which sends drive signals to the stimulator to initiate stimulated contractions and reads logged data from the stimulator unit. The control unit provides drive signals to the stimulator when increased venous return via muscle stimulation is required. Termination of electrical stimulation is triggered when:
(i) for OH syncope, standing for a specified duration has occurred or the patients starts walking
(ii) for POTS syncope, a specified time has elapsed
(iii) for neurocardiogenic syncope, heart rate has restored to desired level.

The stimulator is battery-powered and comprises a control block for running program code and controlling the individual functional blocks of the stimulator, a communication block for facilitating data communication to and from external devices, a memory block for storing programmed parameters, usage data and any other recorded data, a power management block for regulating and monitoring power, a real-time clock to facilitate data logging and stimulus generation circuitry for driving and electrical stimulus electrodes.

The stimulator may be an implanted device or alternatively it may be an external device which applies electrical stimulation transcutaneously through surface electrodes placed on the skin (surface embodiment).

Implanted Stimulator

Figure 2:
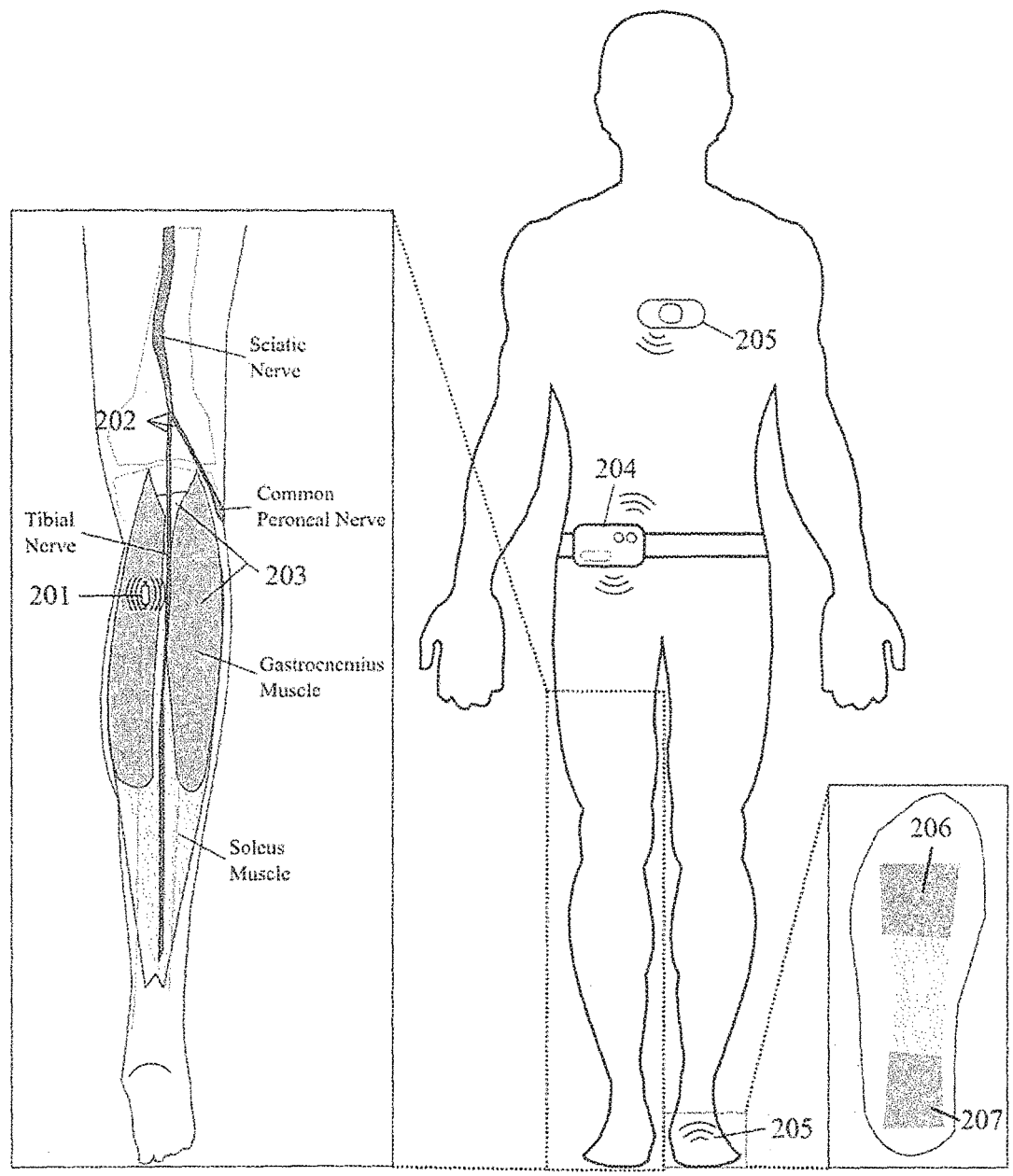
FIG. 2 shows a system of the invention incorporating injectable micro-stimulators.

In one embodiment, injectable micro-stimulators 201 are implanted in the region of motor nerves 202 or muscles 203 which assist with venous return through muscle pumping (FIG. 2). These micro-stimulators are typically self-contained devices, with the electrodes located on the housing of the stimulator device itself and power for the device being provided by a re-chargeable battery incorporated into the device. Drive signals from a control unit 204 trigger stimulation when risk of a syncopal fall is detected based on sensor input from a worn body sensors 205 and sensors incorporated into the control unit 204. The advantage of using injectable, implanted micro-stimulators is that these devices can be implanted in an outpatient setting using a minimally invasive procedure and remove usability issues relating to the need to carry an external stimulator and to correctly place surface electrodes on a daily basis.

Figure 3:
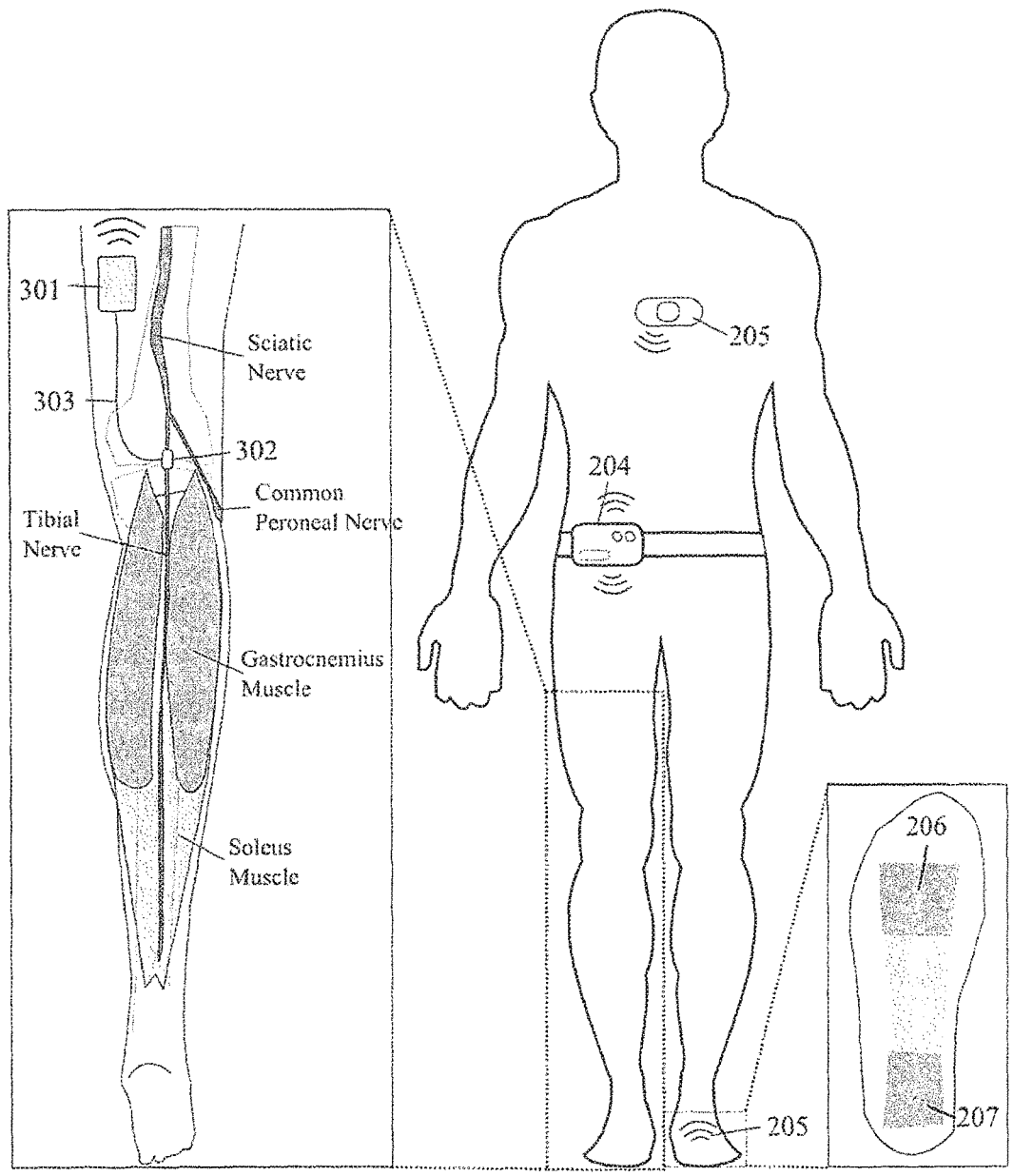
FIG. 3 shows a system of the invention incorporating an implanted stimulator which delivers stimulus to a target nerve via a neural cuff electrode.

Referring to FIG. 3, in an alternative embodiment, the electrodes are in the form of a nerve cuff 302 which is surgically placed around a target nerve for stimulation and connected via an implanted cable 303 to an implanted stimulatus generator 301 which is implanted just below the skin surface near the waist, similar to existing implanted peroneal stimulator devices. Implantable stimulators stimulate the lower leg muscles, which activates the skeletal muscle pump, thereby improving venous return to the heart and preventing syncope. A stimulus generator 301, is connected to the nerve cuff 302 via a multi-lead cable 303. For soleus muscle stimulation, the nerve cuff is placed around the tibial nerve above the knee. The implanted stimulates generator is linked wirelessly to the external body-worn control unit 204. When stimulation is triggered by the control unit under real-time sensor control, the implanted stimulator will stimulate the fascicles of the tibial nerve which will cause contraction of the soleus muscle, thereby improving venous return and preventing Syncope. Ideally, two implanted stimulator devices should be utilised, with a device implanted in both legs to provide maximum venous return from the lower legs. A modified implantable drop foot stimulator (peroneal stimulator) could be utilised for this application. Those skilled in the art will recognise that the implanted stimulator may be repositioned to stimulate a wide variety of muscle groups, including the calf, thigh and abdominal muscles.

An advantageous feature of the system is that the battery-powered micro-stimulator devices are re-charged using ambient techniques with charging circuitry incorporated into the patient's bed so that the implanted stimulator's batteries are re-charged while the patient sleeps without any intervention required by the patient.

Surface Stimulator

Figure 4:
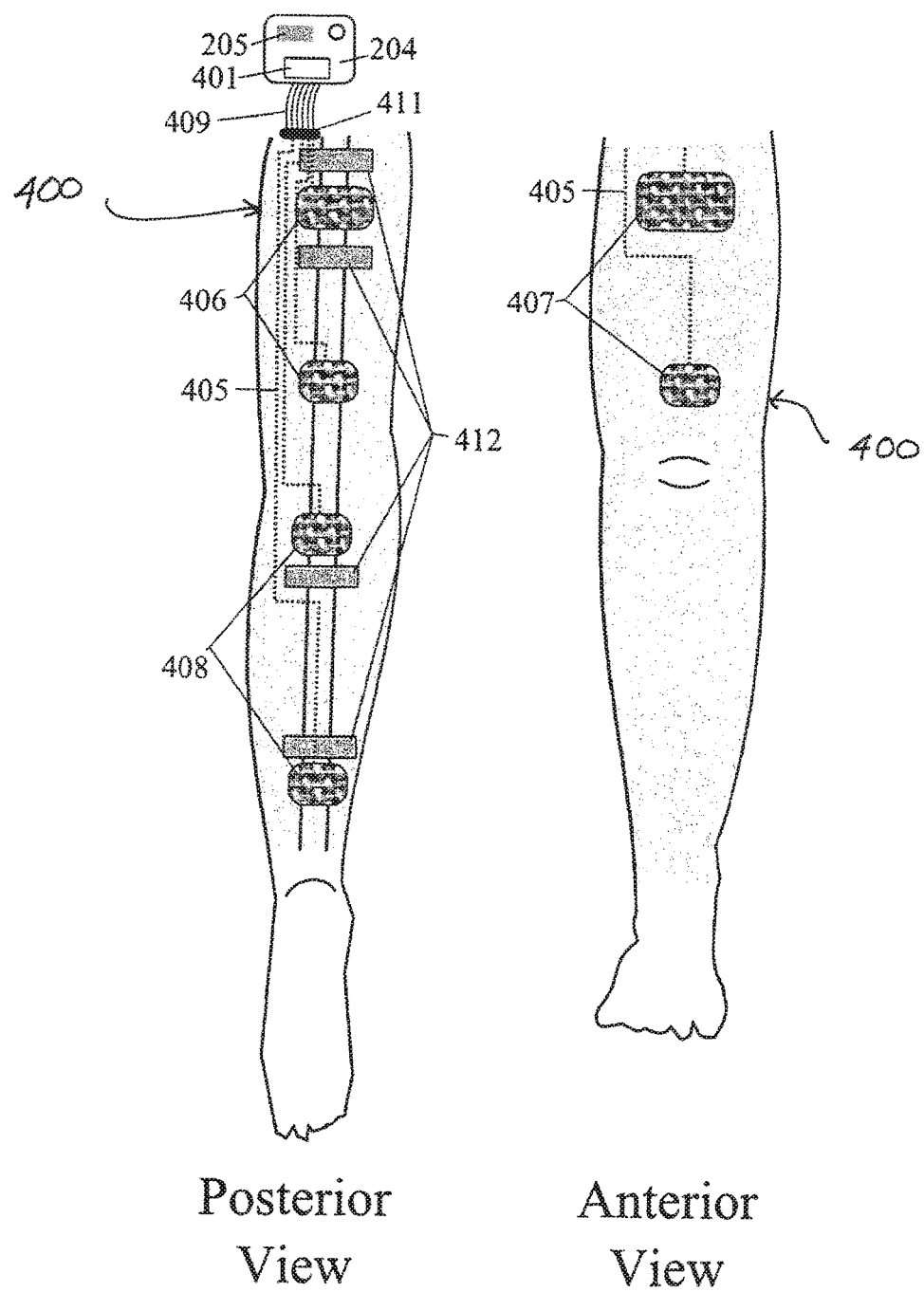
FIG. 4A shows a garment (cuff) to be worn on the leg, incorporating combinations of electrodes for soleus, quadriceps, and hamstring muscle stimulation.
FIG. 4B shows a similar garment to the cuff of FIG. 3A, in which the garment is a stocking, rather than a cuff, incorporating graduated compression.
FIG. 4C shows a garment to be worn on the calf, for soleus stimulation only.
FIG. 4D shows a garment to be worn on the abdomen, incorporating electrodes and a control unit/activity monitor for abdominal muscle stimulation.
Figure 4:
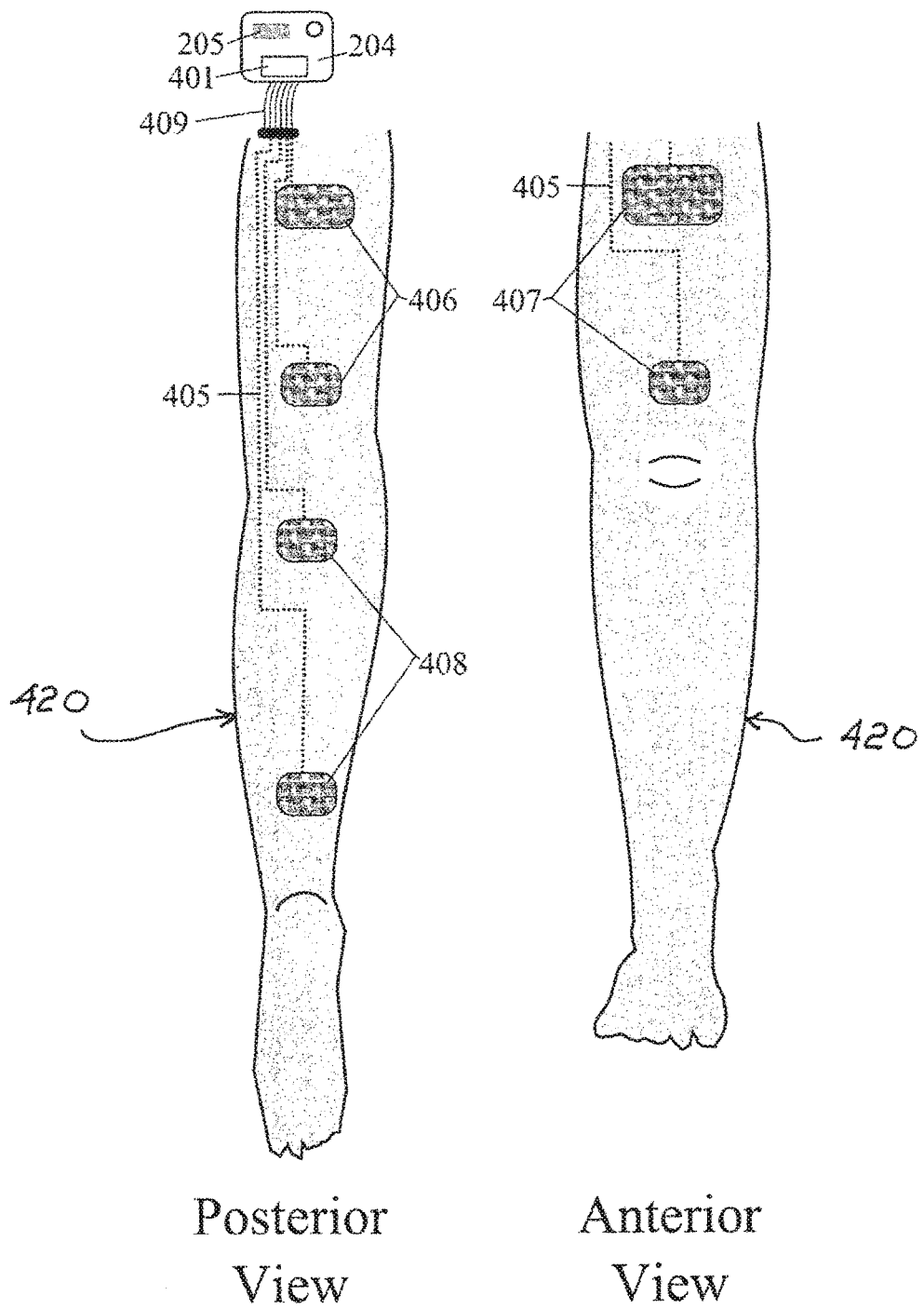
Figure 4:
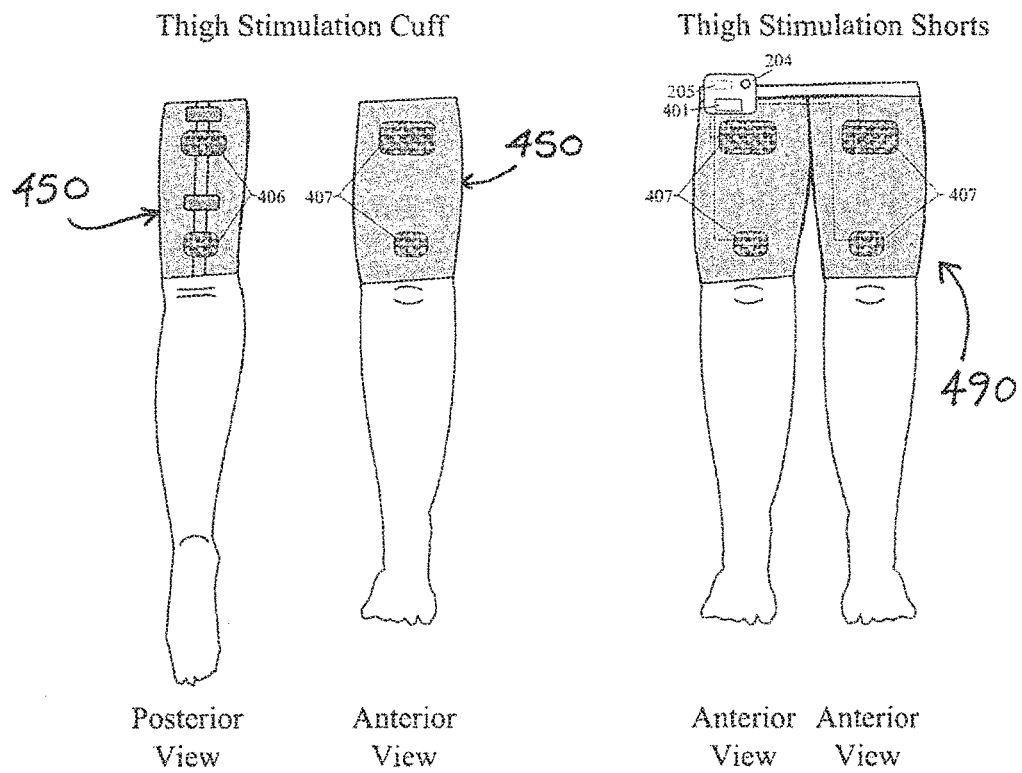
Figure 4:
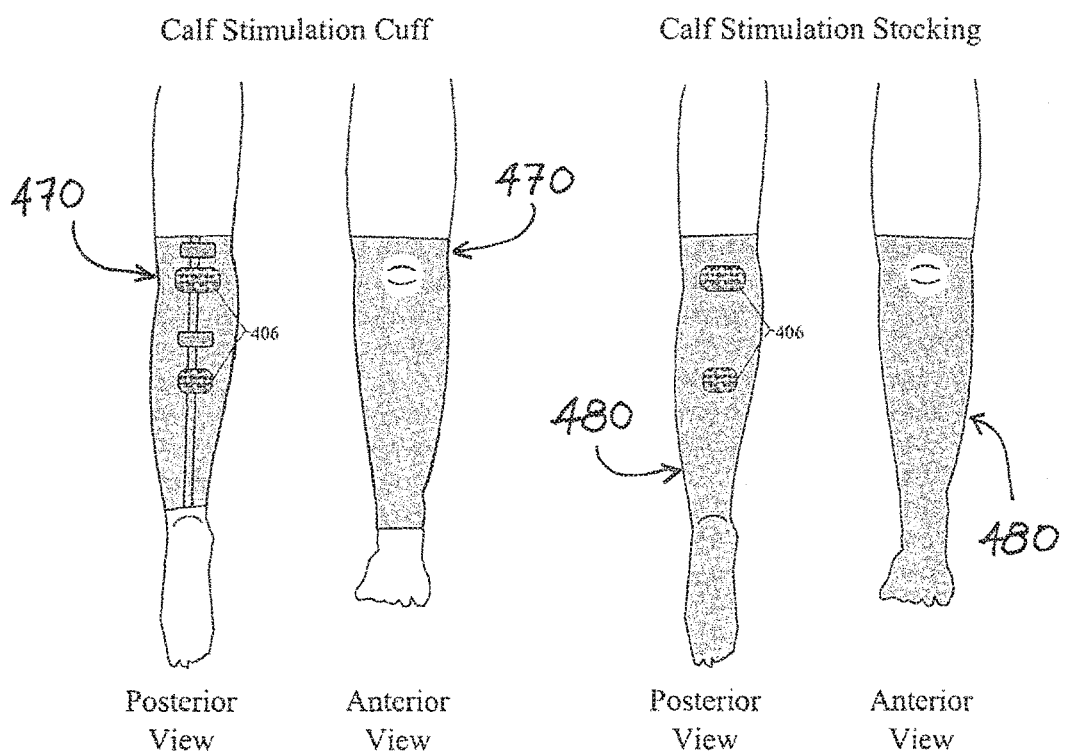

Referring to FIG. 4A, in one embodiment a surface neuromuscular electrical stimulator is used to deliver muscle stimulation via surface electrodes placed on the patient's skin surface over the muscles to be contracted. In this embodiment, kinematic sensors 205 and a surface stimulator 401 can be integrated into the same housing as the control unit 204. The stimulator is connected to electrodes 406, 407, 408) positioned over muscles of the legs (FIG. 4A, FIG. 4B, FIG. 4C) and abdomen (495, FIG. 4D) via a wired connection 405. To ensure correct electrode placement, the electrodes (406-408) could be incorporated into a variety of garments such as a belt for the abdomen (FIG. 4D) or stockings (FIG. 4A), bandages (FIG. 4B) shorts or cuffs (FIG. 4C) for the legs. The housing of the control unit may be worn on the hip, as shown in FIG. 4C, and connected to the electrode leads in the garment via a fabric bus 409. Alternatively, the control unit can be incorporated into the garment itself, where all of the circuitry associated with the control unit is distributed throughout the garment. These drawings also show bio-mechanical sensors 412.

Abdominal Surface Stimulation Example

Figure 4D:
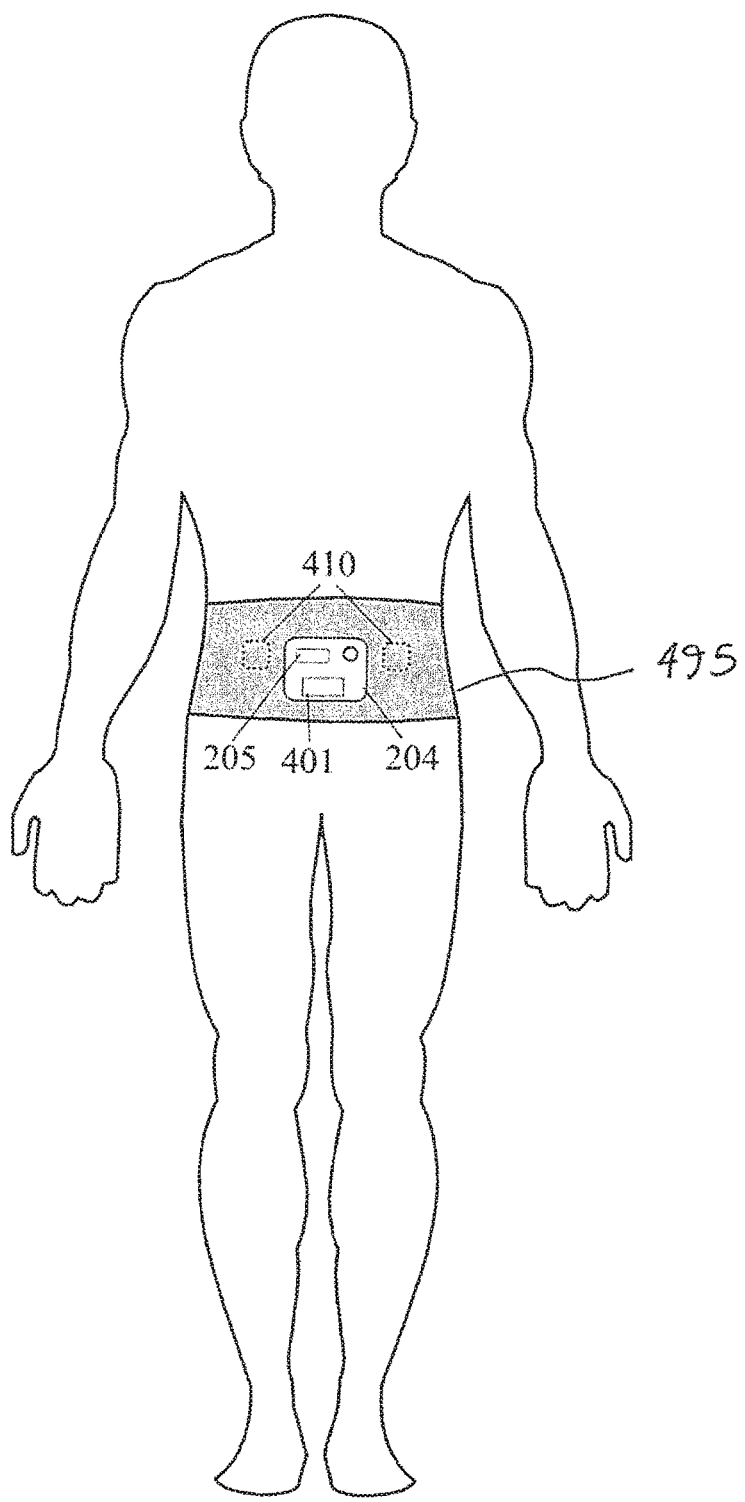

FIG. 4D shows a garment designed to deliver stimulation to the abdominal muscles during posture change or prolonged quiet standing. This garment is worn like a belt around the abdomen, and incorporates electrodes 410 for abdominal stimulation and the control unit 204, with a posture/activity sensor 205 and a stimulus generator 401.

The abdominal veins can act as a blood reservoir in the order of 300 ml that can be released into the circulation. The contraction of abdominal muscles can increase the intra-abdominal pressure, which may squeeze these blood vessels and increase the mean systemic filling pressure and increase venous return; thereby increasing cardiac output.

An increase in the intra-abdominal pressure can hinder the venous drainage of the lower limbs (like in pregnancy and/or in the case of large abdominal tumorous masses). Therefore, abdominal stimulation would be delivered intermittently, to facilitate venous return from the legs. The abdominal stimulator may be used independently, or in combination with lower limb stimulation.

Sensors

A number of measurable parameters are significant for the prediction of syncope. These can be divided into biomechanical parameters and physiological parameters. Biomechanical parameters are used to detect the occurrence of biomechanical events (lying, sitting, prolonged standing, postural transition to an orthostatic posture, physical activity levels and falls) which are significant for monitoring and predicting the onset of syncope (due to a drop in cerebral blood flow during a sit to stand transition). There are six types of biomechanical events which this system aims to detect and measure: posture, intention to change posture, walking, leg activity and the occurrence of falls.

A number of additional measurable physiological parameters have an impact on venous return to the heart, parameters such as respiratory rate and heart rate are also significant inputs. Consequently electrocardiography (ECG) respiratory sensors may help diagnose the cause of a syncopal event.

Garment

To ensure correct stimulation electrode placement on a daily basis, the electrodes could be incorporated into a garment. In the surface stimulation embodiment, the control unit may be worn on the hip, as shown in FIG. 4A, and connected to the electrode leads in the garment via a fabric bus 405. Alternatively, the control unit can be incorporated into the garment itself, by distributing the control unit circuitry into the garment.

The garment (FIG. 4A, 4B, 4C, 4D) is made from hypoallergenic material and incorporates electrodes located within so that they each provide stimulation to the required muscle group when donned. The garment may contain an embroidered or knitted electrically conductive portion to act as an electrode, or separately fabricated electrodes may be attached to the inside of the garment using adhesive or stitching. The electrode wires themselves are of a low profile, flat design with terminals at the top edge of the garment 411. These terminals connect to the stimulation device 401 by a cable 409. Different cable configurations can be made to suit different stimulator devices.

The garment has markings to direct the user to specific anatomical locations to ensure correct positioning of the garment on the limb. Garments for different muscle groups and stimulation sites (FIG. 4A, 4B, 4C, 4D) could be fabricated with the electrodes attached to the appropriate part of the garment to stimulate the desired muscle group. This embodiment has the added benefit that the electrodes help prevent the garment from slipping down.

The garment 400 shown in FIG. 4A contains electrode arrangements for stimulation of the soleus muscle 408, the quadriceps 407, and the hamstring muscles 406. This design allows stimulation to be applied to one muscle group or to combinations of muscle groups in sequence, to produce the maximum effect on venous return. In this embodiment, the garment is a cuff, wrapped around the leg, and fastened onto the leg using Velcro™ straps 412.

In an alternative embodiment shown in FIG. 4B, the garment (420) is implemented as a stocking, which can be unrolled on the user's leg. The stocking 420 contains the same electrode configurations as the cuff garment 400. As well as providing neuromuscular electrical stimulation to the leg muscles, the stocking also incorporates graduated compression, to minimise blood pooling.

In alternative embodiments, the design can be implemented as two separate garments, as shown in FIG. 4C, one designed for calf muscle stimulation only (470), and the other (450) for thigh and hamstring stimulation only. The calf muscle stimulation garment can be implemented as a stocking 480, or as a cuff, 470 as shown in FIG. 4C. The thigh stimulation garment can be implemented as a cuff, stocking, or incorporated into shorts 490 worn by the patient.

The garment should be made from material and designed in such a manner, that when worn around a joint, the garment should be sufficiently flexible so as not to restrict the movement of that joint. Those skilled in the art will recognize that any of the functional blocks of the control unit, sensor unit or stimulation unit may be incorporated into the garment with the use of flexible electronics and conductive textiles.

Sensing of Biomechanical Events

Figure 5:
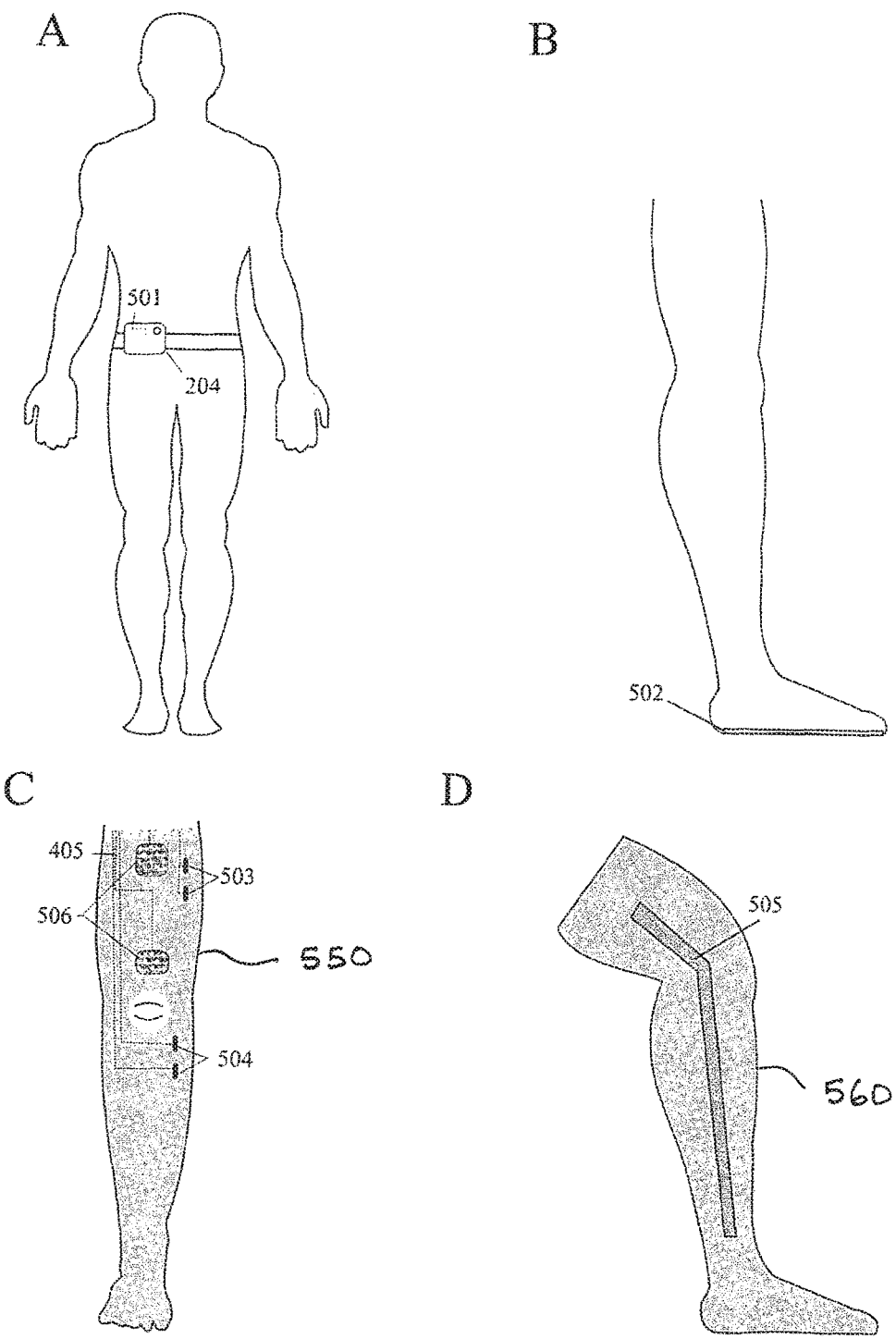
FIG. 5 shows a number of potential posture/activity monitoring sensor arrangements of various embodiments.

FIG. 5 shows a number of sensor systems that can be used to measure posture and physical activity. In one embodiment, shown in FIG. 5A, a kinematic sensor 501 (incorporating accelerometers and gyroscopes) is integrated into a control unit 204, worn on the hip in the trunk segment of the body. Using this methodology, posture transitions and intention to change can be detected by measuring the change in trunk tilt in the saggital plane and by measuring trunk angular velocity in the saggital plan. Positioning the control unit 204 on the thigh would enable the measurement of change in thigh tilt in the saggital plane and thigh angular velocity in the saggital plan. Normal gait causes much greater acceleration (particularly during the heel strike shock impact) than that associated with postural positioning. Motion such as walking can then be simply detected by setting a threshold above which the associated accelerometer signal levels indicate motion/walking. Hence, mobility may easily be distinguished from static postures.

In an alternative embodiment, a footswitch 502 can be used to determine postures and activity, as shown in FIG. 5B). A footswitch is a pressure sensitive switch that is turned on when the patient's weight is applied to the switch during transition to standing, standing, transition to sitting or walking. The footswitch can be implemented as a device which sits in the heel and toe area of the subject's shoe. This sensor arrangement will indicate when force is applied at the heel area and at the toe area or not and when force is applied at both regions and the intensities of these forces in each case. Alternatively, it can be incorporated into a customized insole. In an ideal embodiment the foot switch would incorporate wireless communication circuitry, to facilitate ease of use of the unit. The footswitch can be used independently or in conjunction with the other activity sensor configurations described in FIG. 5.

By combining the use of both a kinematic sensor and foot-switch, the ability to more accurately and reliably detect the precursor event leading to a Syncope is significantly increased as intention to change posture can to detected using both trunk inclination and force applied at the heels and toes. More accurate detection of intention to change posture results in reduced false triggering of NMES (false triggering of NMES when it is not required for Syncope prevention), for instance if a minor change in posture occurs when the person remains sitting. False triggering of NMES due to unreliable detection of precursor events of Syncope must be kept to an absolute minimum as it can be a source of annoyance and discomfort for the patient and could result in system rejection.

FIG. 5C demonstrates a number of sensors 503, 504 that can be incorporated into a leg garment 550. In this example, the control unit is incorporated into the garment itself. The transition from sitting to standing requires significant contraction of the thigh muscles. Posture change can therefore be detected by placing electromyography (EMG) amplifiers 506 over the quadriceps muscles. Posture change is then detected when the EMG signal is greater than a threshold value.

Pairs of accelerometers can also be incorporated into the leg garment above (503) and below (504) the knee. By using two pairs of accelerometers, one pair on the thigh and one pair on the shank, the angle of the knee can be determined by measuring acceleration at these four sensors. This allows posture and posture transitions to be identified i.e. in the seated posture, the thigh is in a horizontal position, and the calf is in a vertical position, and both calf and thigh are vertical during standing. A footswitch 502 (with heel and toe force sensors) can also be integrated into the heel of this garment.

Alternatively, in FIG. 5D, a "smart textile" 505 incorporating electrical sensing elements can be built into a garment 560 to determine kinematic data such as joint angles, from which posture and activity can be determined. Smart textiles can also be used to measure venous pooling.

Pooling of blood in the lower limb causes swelling which will cause stretching of the fabric. This stretching can be detected by smart fabrics woven into the garment.

Sensing of Physiological Events

Heart rate increases are observed in syncope arising from POTS while neurocardiogenic syncope is often accompanied by a sudden reduction in heart rate. Consequently, monitoring of heart rate using ECG electrodes placed on the chest is important for predicting a syncopal fall arising from these conditions. Ideally a single ECG recording device incorporating electrodes is placed on the chest and the R-R interval of the ECG signal is analysed to assess risk or cause of a syncopal fall.

Respiration is significant for monitoring and prediction of syncopal falls as it directly modulates venous return from the lower legs. A respiratory sensor which detects and measures respiratory frequency and tidal volume can help estimate the pressure changes in the thoracic cavity which affects venous return to the heart. Strain gauges and/or fibre optic gauges may be used by the control unit to help determine the risks and causes of a syncopal fall.

Figure 6:
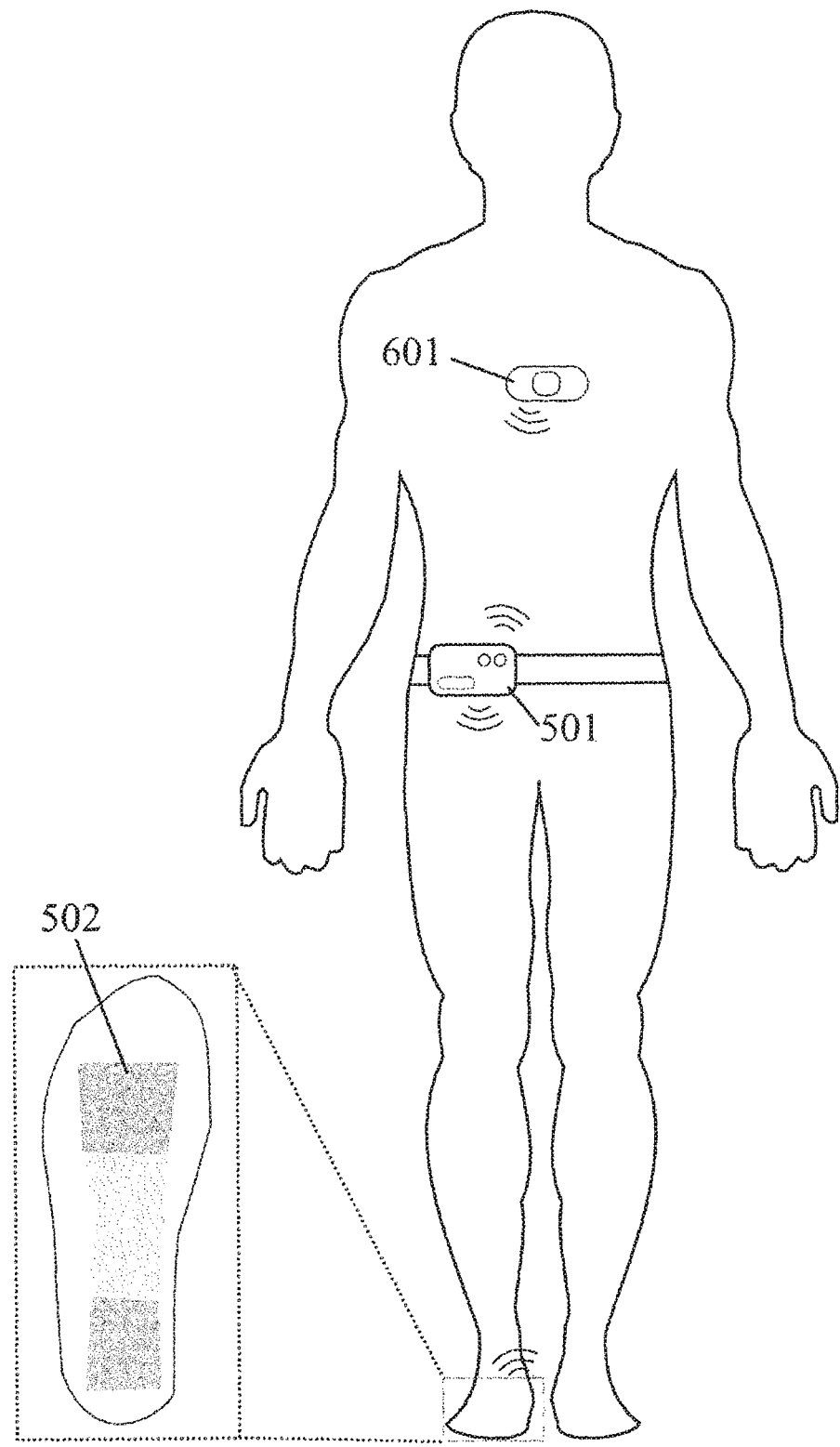
FIG. 6 shows preferred embodiments of the sensor and control elements of the overall system.

In a preferred embodiment (FIG. 6), which achieves sensing and measurement of each of the main biomechanical and physiological events relating to syncope, heart rate is measured using an ECG patch 601 on the chest, while biomechanical events are measured using a combination of a kinematic sensor incorporated into the control unit 501 worn at the hip (on the trunk body segment) and a foot switch 502 under the sole of the foot.

Implanted Sensors

In some circumstances where syncope and increase risk of syncopal falls are expected for the remainder of a person's life, an implanted sensor solution is preferable so that issues with usability and correct application of sensors on a daily basis are not an issue for the patient.

In this instance injectable, implanted accelerometer/EMG/ECG sensors may be used:
(i) for OH syncope to detect the intention to undergo a sit-to-stand transition
(ii) for POTS syncope to detect prolonged quiet standing and heart rate increases
(iii) for neurocardiogenic syncope to detect standing and a sudden decrease in heart rate Those skilled in the art will recognise that a variety of sensor types (accelerometers, piezoelectric sensors, gyroscopes, magnetometers, goniometers, foot switches, smart textiles incorporating electrical sensing elements, ECG sensors, optical or strain gauge sensors), sensor positions (hip, thigh, lower leg, ankle, sole of the foot) and sensor form factors (implanted sensors, external discrete sensors, textile based sensors) can be used alone or in combination with each other to detect and/or measure: intention to change posture, posture, walking, occurrence of falls, leg activity, heart rate and respiratory rate. Depending on the application implanted or non-implanted sensors may be more appropriate. The FIG. 6 system is capable of measuring intention to change posture, posture, walking, occurrence of falls, leg activity and heart rate with a minimal number of sensors, which are non-implanted.

Control Unit

Algorithms in the waist-worn control unit then trigger activation of the surface/implanted stimulator devices, which through neuromuscular electrical stimulation, activate the peripheral muscle pump, with the calf muscle pump typically utilised, thereby increasing venous return to the heart. The waist-worn control unit also records how often the patient is wearing the external unit, how often stimulus is applied and the sensor conditions associated with the delivery of stimulus. While the main purpose of the system is to prevent falls, the waist-worn unit also records fall events if they do occur, as detected by the kinematic sensors described, and if the fall event is detected as being non-recoverable, assistance is automatically and immediately sought from emergency services via a monitoring service. The waist-worn control unit can be charged at the patient's bed-side in a docking station which also transmits the recorded system usage and performance data, via landline telephone network/mobile phone SIM/WiFi, to a data server for analysis by the patient's care-team.

Figure 7:
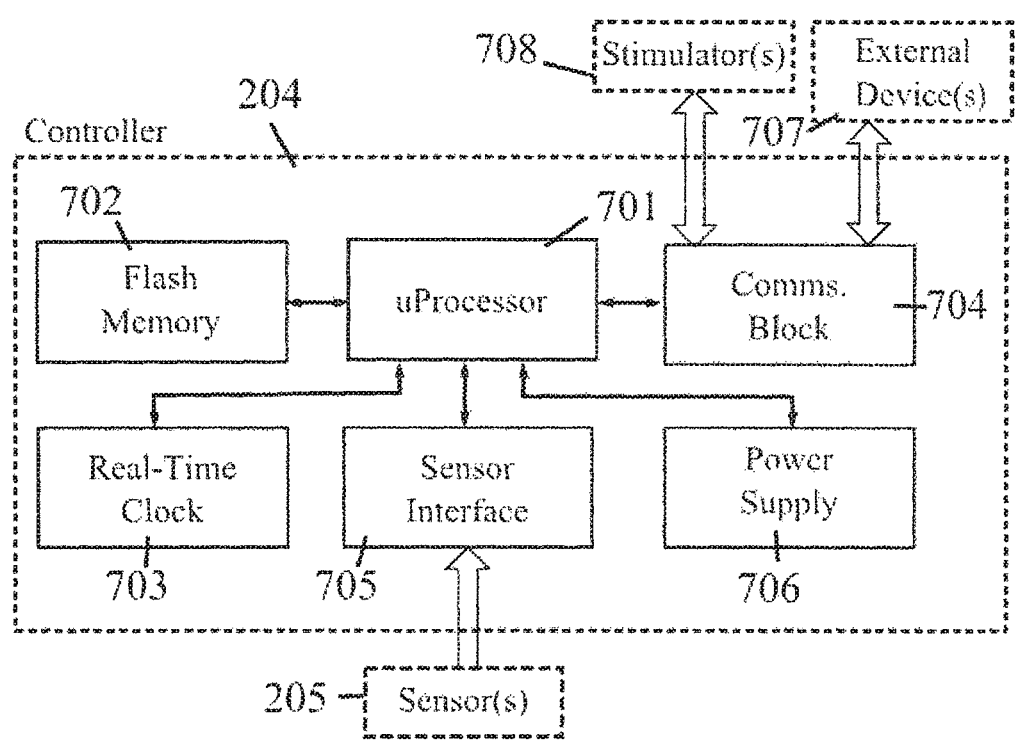
FIG. 7 shows the main functional blocks of a system of the invention.

The posture/activity sensors and the NMES stimulators interface with a control unit, worn by the user. This unit is small and discrete. In the preferred embodiment, the control unit is worn on the user's hip and in this embodiment a kinematic sensor can be incorporated into the device for the measurement of trunk inclination and trunk angular velocity, but may be worn elsewhere or partially incorporated into garments previously described. The control unit also includes a switch or button that will allow the user to manually trigger application of stimulation and/or to turn off stimulation. In the implantable stimulator embodiment, the control unit communicates wirelessly with the implanted stimulator and associated sensors. In the surface stimulator embodiment, the stimulation electronics may be incorporated into the control unit housing 204. In a preferred embodiment (FIG. 7), the control unit comprises:

A microprocessor 701 block for overall control of the system

Flash memory 702 for storing program, sensor, and usage data

A real-time clock 703 for usage monitoring and algorithm detection

A communication block 704 to facilitate wired or wireless communication to external devices 707 including stimulator units 708

A sensor interface 705 to accommodate a range of external and internal sensors 205

Power supply circuitry 706 for regulation of power supply to the device and to facilitate recharging The control unit executes algorithms for triggering NMES stimulation for syncope prevention. These algorithms take posture/activity/foot contact forces and/or heart rate/physiological data as input, and trigger NMES stimulation based on subject activity and physiological state. The control unit can also as an additional support feature for the patient contain algorithms for fall detection in the event of a syncopal fall, so that an alert may be sent to the care-giver or emergency services.

An advantageous feature of the system is that the battery-powered waist-worn control unit is re-charged using ambient techniques with charging circuitry incorporated into the patient's seating furniture, for example arm-chair so that the re-chargeable battery of the waist-worn control unit is re-charged while the patient sits without any intervention by the patient.

Control Unit Algorithms

Orthostatic Hypotension

Figure 8:
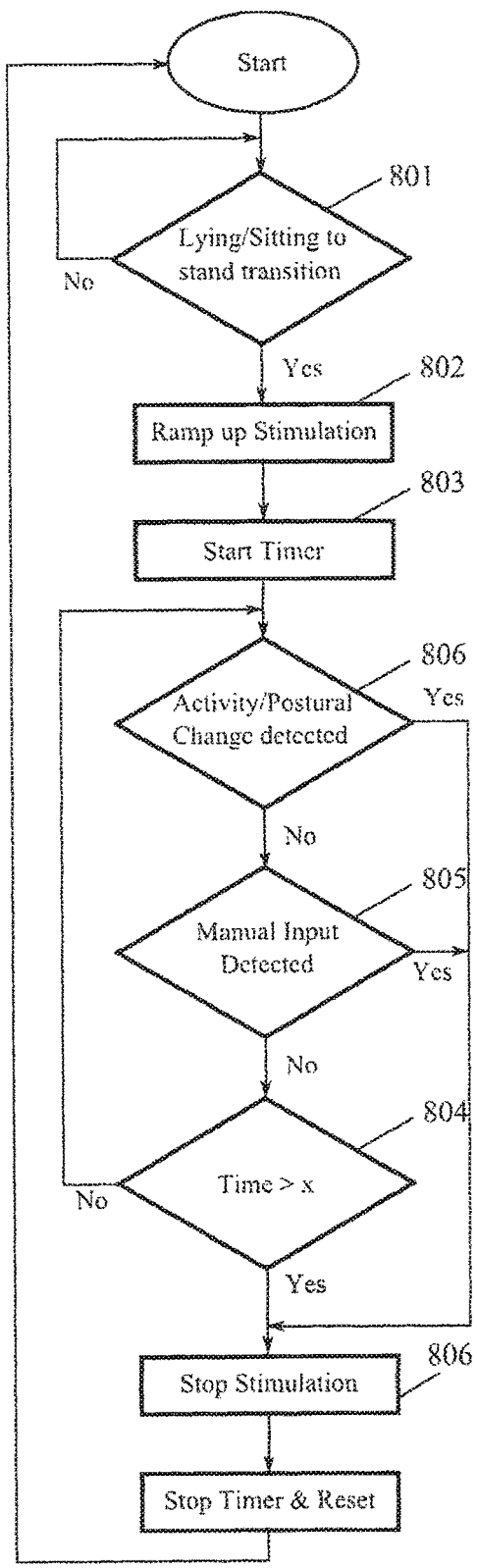
FIG. 8 shows a program flow chart for an OH algorithm of a system control unit.

With reference to FIG. 8, for prevention of syncope due to orthostatic hypotension, stimulation is triggered when the algorithm detects an intention to change in posture. Upon detecting intention to assume an upright posture (801), the control unit triggers neuromuscular electrical stimulation (802) by sending drive signals to the stimulator(s), causing contraction of the target muscles, thereby increasing venous return and therefore cardiac output. Once stimulation has commenced a timer is started (803) and stimulation will continue to be applied until the timer reaches a preset value (804). Stimulation is stopped (807) if the timer has not reached its predefined value and the user manually interrupts stimulation (805) or user initiation of walking is detected by the sensor unit (806). NMES is then turned off, leaving the patient free to ambulate. In the example in FIG. 6, stimulation is applied to the soleus muscles via an implanted stimulator. However, stimulation can be applied either by implanted or surface means to any of the muscle groups previously described.

In the event of an emergency a waist-worn control unit issues an alert via Bluetooth to the docking station, which relays this alert to the external emergency monitoring service. A SIM card could also be incorporated into the waist-worn control unit to allow direct communication between the unit and a data server or an external emergency monitoring service.

Postural Orthostatic Tachycardia Syndrome (POTS)

The skeletal muscle pump is a key defense mechanism for maintaining venous return and blood pressure during upright posture. The act of walking activates the skeletal muscle pump. During periods of prolonged quiet standing (at a programmable interval set by the clinician), the skeletal muscle pump is inactive, and blood can pool in the veins of the abdomen and lower limbs. This phenomenon is exaggerated in POTS and can lead to fainting and injuries.

Figure 9:
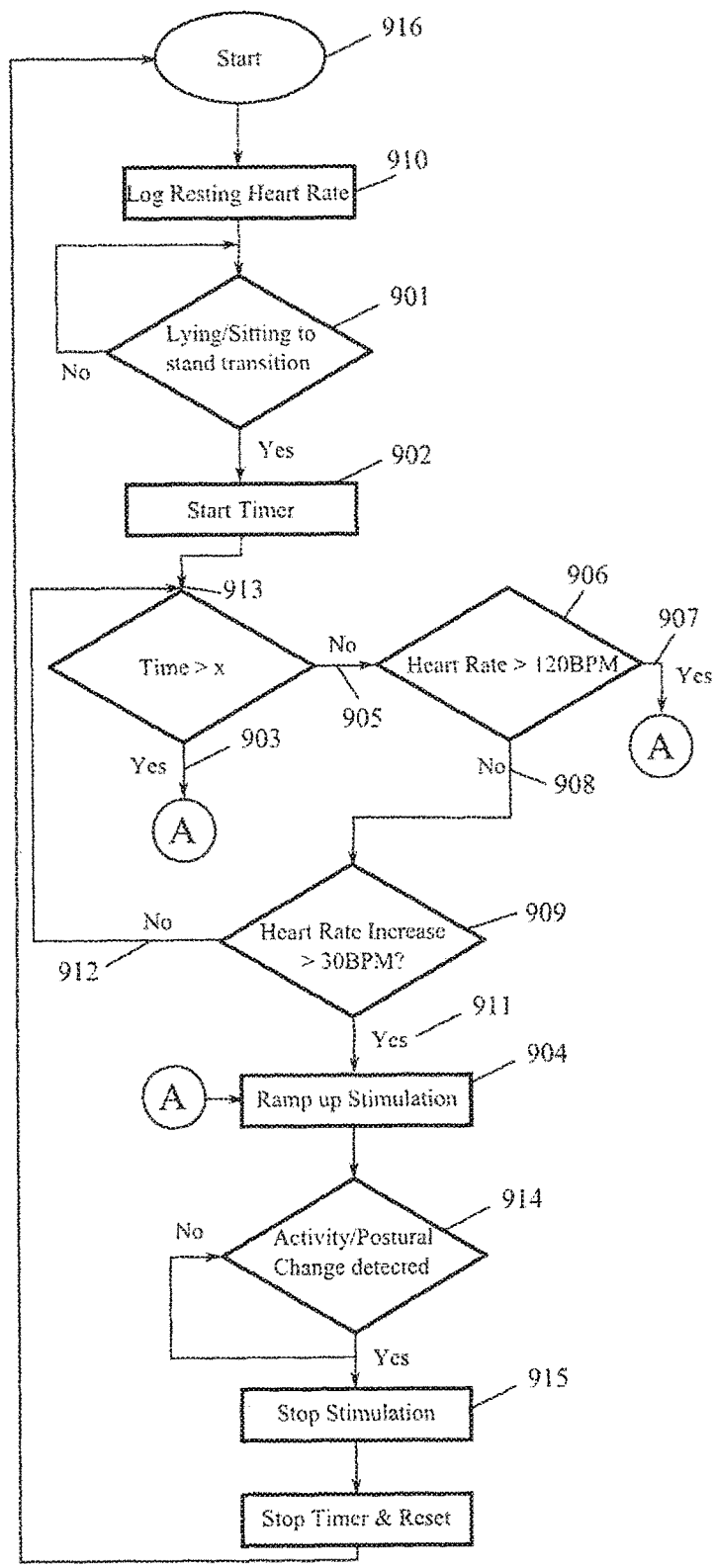
FIG. 9 shows a program flow chart for a POTS algorithm of a system control unit.

The POTS algorithm works by applying NMES when a prolonged period of standing has been detected. With reference to FIG. 9, when a standing posture is detected (901), a timer starts counting (902) to a patient specific value which, when reached is indicative of a prolonged period of standing which may results in venous pooling and risk of a syncopal fall. Once this time has been exceeded (903) NMES is applied intermittently to reduce venous pooling and promote venous return (904). POTS patients also experience an exaggerated increase in heart rate during upright posture. If the timer value has not been reached (905) the algorithm checks for a sustained heart rate above 120 beats per minute (906) and applies NMES (904) if a heart rate above 120 beats per minute is detected (907). If a heart rate above 120 beats per minute is not detected (908) then the algorithm checks for an increase in heart rate of 30 beats per minute (909) above the pre-transition resting heart rate (910). If the heart rate increase is greater than 30 beats per minute (911) then NMES is applied (904). If the heart rate is not found to be greater than 30 beats per minute (912) than the algorithm returns back to the start of the timer checking step (913).

Once NMES has started the algorithm checks for initiation of walking, a postural change from an orthostatic posture to one which does not pose a risk of a syncopal fall (e.g. sitting or lying) (914). If such activity or transitions are detected than NMES ceases (915) and the algorithm is reset to its starting state (916). The algorithm may be interrupted at any point by initiation of walking which will cause NMES to stop, the timer to be reset and the algorithm to return to its resting state.

Neurocardiogenic Syncope

A third algorithm also analyses heart rate information to determine whether or not NMES should be applied for the prevention of falls as a result of neurocardiogenic syncope. Many neurocardiogenic syncope patients, during standing, often experience a sudden onset, rapid drop in heart rate before fainting. If a sudden drop in heart rate is detected, the subject will be warned that stimulation is about to be applied. The warning could take the form of an audio or tactile cue (i.e. a beep, or vibration), or by providing stimulation for a short duration, at a level that the patient can feel, but not strong enough to cause a full contraction. Full stimulation of skeletal muscles will then be applied, to augment venous return and prevent syncope.

It should be noted that, in the invention, the leg muscles are not stimulated during walking. However, abdominal stimulation may be applied during walking if the changes in heart rate previously described are identified.

Those skilled in the art will recognise that other physiological data may be used to trigger stimulation. These data include excessive pooling of blood in the lower limb (measured by smart textiles woven into a garment, or by impedance plethysmography), respiratory data, increased perspiration, autonomic nervous system activity (e.g. from heart rate variability), and blood pressure data.

Fall Algorithm

Figure 10:
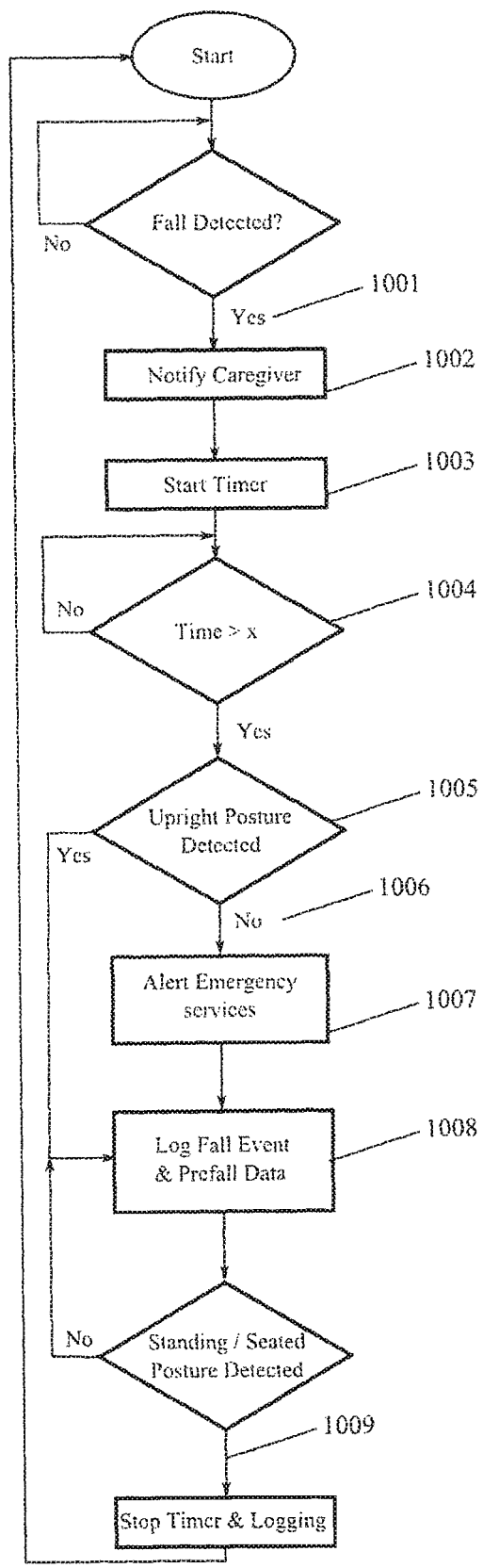
FIG. 10 shows a program flow chart for a fall detection algorithm for a system control unit.

The systems of the invention act to prevent syncopal falls. However, in some embodiments the system also acts to detect falls if they occur, thereby generating alerts so that the patient is attended to as quickly as possible. The time lag before assistance can be critical in many circumstances. With reference to FIG. 10, the kinematic sensor device used to detect posture transition/postures can also be used to detect patient falls if they occur by measuring the shock impact during a fall and can determine if the fall is a recoverable fall by measuring the patient's posture post impact. If a fall is detected (1001), the patient's primary care-giver is notified (1002) and a timer is started (1003) to quantify the length of time it takes for the patient to change posture post-impact (1005). The timer then counts up to a predefined time period (1004). If the patient doesn't change posture within this time period (1006) then the fall is deemed non-recoverable and emergency services are alerted (1007). Once all of the necessary alerts have been raised the algorithm logs the time, date, time spent in the post-impact posture and also logs the pre-impact and post-impact time-stamped, sensed data (physiological & biomechanical events) (1008), the algorithm is reset and data logging stopped only when the user has recovered to a standing or seated posture (1009). The logged pre-fall data is used to automatically alert emergency services in the event of a non-recoverable fall and the logged sensor data surrounding the fall is transmitted to the care team as part of the described reporting system in the event of a recoverable fall. Alternatively, the logged data can be used to adjust preset thresholds and provide training data to enhance the predictability of syncopal events. Those skilled in the art will recognize that a variety of thresholds and timing parameters may be used to detect the occurrence of a fall.

State Machine Algorithm

Referring to FIG. 12 operation of a processor in the control unit of one embodiment is illustrated. It uses the finite state machine paradigm. NMES outputs are generated for an OH patient when the precursor for syncope occurs—postural change from lying to sitting or standing NMES outputs are generated for a POTS patient when the precursors of prolonged quiet standing AND/OR (Heart Rate (HR)>120 BPM (Beats per Minute) OR an increase in HR of 30 BPM) occur.

The algorithm uses a waist worn accelerometer and gyroscope combination to determine trunk inclination (degrees) and trunk angular velocity (rads/sec) and toe and heel foot-switches to determine heel and toe contact forces (as % B.W.) and a chest worn ECG patch to measure heart rate and heart rate changes.

The abbreviations used are:
tol, tolerance
+ive, positive
−ive, negative
up arrow, increasing
down arrow, decreasing
θ, angular displacement
ω, angular velocity
B.W., body weight
Δ, change As illustrated, the major states detected are: lying state, lie-to-sit transition state, sitting with feet horizontal, sitting with feet on ground, sit-to-stand transition, and standing. The processor uses a range of sensory inputs, both biomechanical and physiological.

This state-machine based algorithm is designed to run in real-time with a computationally straight-forward data analysis of sensor data from a trunk worn kinematic sensor, heel & toe foot-switches and a heart rate sensor. Algorithm execution speed on the embedded portable electronics incorporated into the control unit is such that NMES can be delivered in sufficient time after the detection of the precursor event to prevent syncope.

The algorithm is designed to execute quickly in real-time using these sensor inputs to detect the precursor events to OH Syncope and to in response to the detection of these precursor event to deliver NMES and activate the muscle pumps to prevent the OH syncope event from occurring. The state-machine based algorithm minimises inadvertent application of NMES while also delivering NMES appropriately to prevent syncope and to operate in real-time.

POTS syncope is triggered by prolonged quiet standing and thus the precursor event to POTS syncope is prolonged quiet standing. The same sensor setup for OH syncope can be used for POTS syncope—the state machine algorithm will detect when the person is standing and whether or not they are engaged in prolonged quiet standing. As is clear from the bottom of FIG. 12 the physiological sensory input of heart rate (HR) contributes to a determination of risk of POTS-type syncope.

Also, it will be appreciated from FIG. 12 that the processor advantageously defines physical postures of the patient as finite state machine states, namely lying, sitting with feet horizontal, sitting with feet on the ground, and standing. It also defines transitions as states, namely lie-to-sit and sit-to-stand transitions.

The states illustrated in FIG. 12 are used by the processor to determine the extent and timing of NMES activation. This is especially so because it associates NMES activation permissions with particular states. In the lying state the patient is not at risk of syncope therefore this state is associated with the non application of NMES. In the lie to sit transition state, the person is typically in the process of sitting up in the bed and again this state is associated with the non-application of NMES. In the sitting with the feet horizontal state, the patient is typically sitting up in the bed and application of NMES is not required. In sitting with the feet on the ground state, the user is in a posture which is much closer to standing and thus as a precautionary measure the processor applies NMES when the patient is in this state but at 50% of the intensity that would occur during the sit-to-stand transition state. In the sit-to-stand transition state the user is in the critical state for the prevention of syncope and NMES is delivered at 100% of the final intensity to be applied to fully activate the muscle pumps. In the standing state the system maintains NMES until the patient has stabilised in this state and NMES is applied at 100% intensity and a patient-specific timer is run. When this timer expires or the patient starts walking (whichever occurs first), NMES is turned off.

The overall goal of the state machine based algorithm is the robust detection of those states in which NMES needs to be delivered and the robust identification of those states when NMES does not need to be delivered. To achieve maximum comfort for the patient and to avoid un-necessary application of NMES to the patient, the algorithm is designed carefully to only apply NMES when required to prevent syncope. This is achieved by identifying the full series of states associated with going from a lying to a standing posture and targeting the delivery of NMES only in those states where it is required. In particular the algorithm breaks down the process of assuming an upright posture into a series of steps so that NMES is only delivered when absolutely necessary to prevent syncope and avoids as much as possible un-necessary application of NMES.

By using multiple sensors (which have been carefully chosen to be as unobtrusive as possible and to not impede the patient carrying out their normal activities of daily living) the risk of incorrectly identifying a state in the algorithm's state machine is greatly reduced For example if only the trunk inclination was used to detect an upright posture, a person sitting up in a bed would have NMES applied, by adding heel and toe foot switches, the system can distinguish between sitting up in bed (NMES not needed) and sitting in the manner one would sit in a chair (start the process of applying NMES at 50%). If trunk inclination and trunk angular velocity were used, the detection accuracy is improved. Then, if trunk inclination, trunk angular velocity, heel contact force and toe contact force are used high levels of detection accuracy are achieved.

An advantageous feature of the system is the use of low-pass filtering of sensor outputs, such as trunk inclination, trunk angular velocity, heel contact force and toe contact force prior to the signals being input to the algorithm. The purpose of this filtering to eliminate rapid changes in these signals, which represent spurious activity, such as tapping the heel on the ground when sitting, and which if unfiltered may cause the algorithm to rapidly move in and out of adjacent state machine states and thus potentially cause inadvertent cycling between the application of NMES and the non-application of NMES. The accelerometer and gyroscope signals can typically be low pass filtered very conveniently in hardware by the addition of a capacitor to the output of the device. The cut-off frequency to be utilised may be in the order of 5 Hz. Each accelerometer, gyro, or other sensor typically has a particular preferred cut-off frequency. The cut-off frequency may be set to reflect the patient's unique movement characteristics. Low pass filtering of the foot-switch signals would be implemented using an active low pass filter in hardware and again a cut-off frequency of the order of 5 Hz would be adequate for most applications, and more generally preferably in the range of 3 Hz to 7 Hz. The low pass filtering could also be implemented in software using moving average techniques with the moving average window size determining the cut-off frequency—the greater the number of samples in the window, the lower the cut-off frequency.

State Detection in the State Machine Algorithm:
Lying State
Patient is lying horizontal, feet are not making contact with the ground, there can be some trunk inclination but if there is no foot contact, clearly the person is lying.
Trunk Inclination=0°±tolerance
AND
Trunk Angular Velocity=0 rads/s±tolerance
AND
Heel Contact Force=0% Body Weight (BW)±tol
AND
Toe Contact Force=0% Body Weight (BW)±tol
Output: NO NMES
Lie-to-Sit Transition State
Patient is assuming the sitting up position (in bed) with feet on bed and not making contact with ground.
Trunk Inclination>45°±tolerance
AND
Trunk Angular Velocity=+ive
AND
Heel Contact Force=0% Body Weight (BW)±tol
AND
Toe Contact Force=0% Body Weight (BW)±tol
Output: NO NMES
Sitting with Feet Horizontal State
Patient is assuming the sitting up position (in bed) with feet on bed and mot making contact with ground.
Trunk Inclination=90°±tolerance
AND
Trunk Angular Velocity=0 rads/s±tol
AND
Heel Contact Force=0% Body Weight (BW)±tol
AND
Toe Contact Force=0% Body Weight (BW)±tol
Output: Person could just plan to be sitting on the bed for an extended period therefore it not be appropriate to apply muscle stimulation⇒NO NMES
Sitting with Feet on Ground State
Patient is sitting with feet making contact with the ground
Trunk Inclination=90°±tolerance
AND
Trunk Angular Velocity=0 rads/s±tol
AND
Heel Contact Force>10% Body Weight (BW)±tol
Output: Step 1 of Assuming Upright Posture⇒Apply NMES at 50% of Final Intensity to be applied to initiate the activation of the calf muscle pump but not at full strength.
Sit-to-Stand Transition State
Patient starts the transition from sitting to standing
Trunk Inclination>=90°±tolerance
AND
Heel Contact Force>20% Body Weight (BW)±tol AND increasing
Output: Step 2 of Assuming Upright Posture⇒Apply NMES at 100% of Final Intensity to be applied to fully activate of the calf muscle pump.
Standing State
Patient is fully upright
Trunk Inclination=90°±tolerance
AND
Trunk Angular Velocity 0 rads/s±tol
AND
Heel Contact Force>10% Body Weight (BW)±tol
AND
Toe Contact Force>10% Body Weight (BW)±tol
Output: Step 3 of Assuming Upright Posture⇒Apply NMES at 100% start timer for patient specific timer duration (in the order of 30 seconds), turn off NMES when timer ends or when patients starts walking, which ever occurs first.
Usage Reporting
In one embodiment, when stimulation has been triggered, a summary of usage data will automatically be transmitted (via WiFi or cell phone network etc) to a data server for analysis.

Alternatively, usage data could be stored in memory on the control unit. Usage data could then be downloaded by plugging the control unit into a cradle. This cradle could be connected to a PC, or transmit data directly to a server via WiFi or broadband link. These data could also be printed directly from the PC via a software interface. This cradle could also be used to charge the control unit battery at night, while the system is not in use.

Usage Data May Include:
Dates and time when stimulation application occurred
Patient activity that triggered stimulation (posture change, abnormal heart rate, prolonged standing, manual trigger)
Heart rate reading and/or other physiological data values that triggered stimulation
Kinematic sensor data
Foot-switch data
Incidence of falls and data logged pre and post-impact.

This information is stored on a secure database, which can be accessed by the patient's physician. The offline data can be analysed to assess the effectiveness of the system, user compliance, and monitor patterns of patient activity. This information could be analysed for research purposes, or could be used by the clinician to assess the effect of the system on the user's quality of life.

Those skilled in the art will recognise that additional features may be added to the control unit, for example, the use of GPS to monitor patient location and mobility.

Pilot Data
Pilot data has been obtained using NMES calf muscle stimulation during head upright tilt table testing with OH patients. Two elderly patients (one male, one female) with OH diagnosed by head upright tilt test were recruited. Each patient performed a control tilt table test with no intervention, and a tilt test with NMES stimulation applied to the calf muscles during head upright tilt. The order of testing was randomised.

In both cases, NMES calf muscle stimulation significantly reduced the postural drop in blood pressure during head upright tilt. In the first patient, postural drop in blood pressure was reduced from 31/27 mmHg (systolic/diastolic) to 13/15 mmHg, and in the second patient, the postural drop was reduced from 35/8 mmHg to 23/11 mmHg. The response of one patient is shown in FIG. 11.

While the invention has been described above in connection with one particular embodiment and example, one skilled in the art will appreciate that the invention is not necessarily so limited. It will thus be understood that numerous other embodiments, examples, uses, modifications of, and departures from the invention disclosed may be made without departing from the scope of the present invention as claimed herein.

The invention is not limited to the embodiments described but may be varied in construction and details.

The invention claimed is:

1. A method for monitoring a user, the method being performed by a monitoring system having at least one bio-mechanical sensor and/or at least one physiological sensor, the at least one bio-mechanical sensor and/or the at least one physiological sensor including at least one implantable sensor selected from:
   an accelerometer,
   an electrocardiography sensor,
   an electromyography sensor, and
   a gyroscope,
   an output device including an implantable stimulator, and
   a controller having a signal conditioning circuit and a processor arranged to receive sensory inputs from the sensors and to execute algorithms to provide output signals for the output device,
   the implantable stimulator including a nerve cuff and the processor being configured to provide output signals to said nerve cuff, the method comprising:
      detecting from the at least one bio-mechanical sensor and/or the at least one physiological sensor a user posture or a user posture transition, and an intention of a sit-to-stand posture transition and using said detection to determine risk of a syncopal event, and
      providing output signals to said output device to prevent a syncopal event from occurring,
      including providing output signals to said implantable stimulator for directly stimulating skeletal muscle or a nerve thereof for skeletal muscle stimulation to increase venous return by contraction of skeletal muscles.

2. A method for monitoring a user, the method being performed by a monitoring system having at least one bio-mechanical sensor and/or at least one physiological sensor, the at least one bio-mechanical sensor and/or the at least one physiological sensor including at least one implantable sensor selected from:
   an accelerometer,
   an electrocardiography sensor,
   an electromyography sensor, and
   a gyroscope,
   an output device including an implantable stimulator, and
   a controller having a signal conditioning circuit and a processor arranged to receive sensory inputs from the sensors and to execute algorithms to provide output signals for the output device,
   the system including electromyography amplifiers adapted to be located over a patient's quadriceps muscles, and the processor determining said intention of a sit-to-stand posture transition when an electromyography signal is greater than a threshold value,
   the method comprising:
      detecting from the at least one bio-mechanical sensor and/or the at least one physiological sensor a user posture or a user posture transition, and an intention of a sit-to-stand posture transition and using said detection to determine risk of a syncopal event, and
      providing output signals to said output device to prevent a syncopal event from occurring,
      including providing output signals to said implantable stimulator for directly stimulating skeletal muscle or a nerve thereof for skeletal muscle stimulation to increase venous return by contraction of skeletal muscles.

3. A method for monitoring a user, the method being performed by a monitoring system having at least one bio-mechanical sensor and/or at least one physiological sensor, the at least one bio-mechanical sensor and/or the at least one physiological sensor including at least one implantable sensor selected from:
   an accelerometer,
   an electrocardiography sensor,
   an electromyography sensor, and
   a gyroscope,
   an output device including an implantable stimulator, and
   a controller having a signal conditioning circuit and a processor arranged to receive sensory inputs from the sensors and to execute algorithms to provide output signals for the output device,
   the processor being configured to output signals to drive said at least one stimulator located in a patient's thigh,
   the method comprising:
      detecting from the at least one bio-mechanical sensor and/or the at least one physiological sensor a user posture or a user posture transition, and an intention of a sit-to-stand posture transition and using said detection to determine risk of a syncopal event, and
      providing output signals to said output device to prevent a syncopal event from occurring,
      including providing output signals to said implantable stimulator for directly stimulating skeletal muscle or a nerve thereof for skeletal muscle stimulation to increase venous return by contraction of skeletal muscles.

* * * * *